United States Patent [19]

Chihiro et al.

[11] Patent Number: 5,639,770
[45] Date of Patent: Jun. 17, 1997

[54] THIAZOLE DERIVATIVES

[75] Inventors: Masatoshi Chihiro, Naruto; Hajime Komatsu, Tokyo; Michiaki Tominaga, Itano-Gun; Yoichi Yabuuchi, Tokushima, all of Japan

[73] Assignee: Otsuka Pharmaceutical Co., Ltd., Tokyo, Japan

[21] Appl. No.: 570,187

[22] Filed: Dec. 11, 1995

Related U.S. Application Data

[63] Continuation of Ser. No. 182,001, filed as PCT/JP93/00700, May 26, 1993, published as WO93/24472, Dec. 9, 1993, abandoned.

[30] Foreign Application Priority Data

May 29, 1992 [JP] Japan .................... 4-138165

[51] Int. Cl.$^6$ .................. A61K 31/425; C07D 277/22
[52] U.S. Cl. .................. 514/365; 544/63; 544/133; 544/364; 544/369; 544/405; 546/269.7; 548/110; 548/144; 548/202; 548/203; 548/204
[58] Field of Search .................. 548/202, 203, 548/204, 144, 110; 546/280; 544/369, 405, 133, 63, 364; 514/365

[56] References Cited

U.S. PATENT DOCUMENTS

| | | | |
|---|---|---|---|
| 1,970,656 | 8/1934 | Johnson | 260/44 |
| 3,821,237 | 6/1974 | Malen et al. | 260/302 |
| 4,001,420 | 1/1977 | Malen et al. | 424/270 |
| 4,791,200 | 12/1988 | Press | 544/369 |

FOREIGN PATENT DOCUMENTS

| | | |
|---|---|---|
| 0 037 710 A1 | 10/1981 | European Pat. Off. . |
| 0 167 973 A1 | 1/1986 | European Pat. Off. . |
| 0 234 729 A2 | 8/1987 | European Pat. Off. . |
| 0 310 370 A1 | 4/1989 | European Pat. Off. . |
| 0 513 387 | 6/1992 | European Pat. Off. . |
| 1 962 493 | 6/1970 | Germany . |
| 30 26 054 | 2/1981 | Germany . |
| B-46-15935 | 4/1971 | Japan . |
| A-47-1469 | 1/1972 | Japan . |
| A-54-61936 | 5/1979 | Japan . |
| A-55-11579 | 1/1980 | Japan . |
| 55-133366 | 10/1980 | Japan . |
| A-60-230147 | 11/1985 | Japan . |
| A-61-40276 | 2/1986 | Japan . |
| 61-167685 | 7/1986 | Japan . |
| A-62-22493 | 1/1987 | Japan . |
| A-63-192755 | 8/1988 | Japan . |
| A-2-171280 | 12/1988 | Japan . |

OTHER PUBLICATIONS

Chemical Abstracts, vol. 82, (25), 170971c (1975), p. 549.
Chemical Abstracts, vol. 109, (3), 109:22883m (1988), p. 610.
Chemical Abstracts, vol. 66, (22), 96203e (1967), p. 9037.
Chemical Abstracts, vol. 71, (23), 112921y (1969), p. 381.
Chemical Abstracts, vol. 86, (9), 86:55326 (1977), p. 430.
Chemical Abstracts, vol. 96, (3), 96:20015u (1982), p. 444.
Chemical Abstracts, vol. 85, (21), 85:159962s (1976), p. 538.
"Synthesis and Antibercular Activity of 4-(5-Nitro-2-furyl-2-pyrazinyl/1-adamantyl)-2-(alkyl/Aryl/arylamino)thiazoles", B.G. Khadse et al., Indian Journal of Chemistry, vol. 26B, Sep. 1987, pp. 856-860.
Pat.l, J. Indian Chem Soc. 56 (12) 1243 1979 Abstract Only.
Chaudhari, Bull. Haffkine Inst 1975 3(2) pp. 81-90 Abstract Only.
"Thiazole Derivatives", S.N. Sawhney et al., Indian Jounnal of Chemistry, vol. 15B, Aug. 1977, pp. 727-730.
J. Prakt. Chem., 325, (4), pp. 551-560 (1983).
Chemical Abstracts, vol. 101, (1), 101:7145p (1984).
Chemical Abstracts, vol. 94, (3), 94: 15628a (1981).

*Primary Examiner*—Robert Gerstl
*Attorney, Agent, or Firm*—Finnegan, Henderson, Farabow, Garrett & Dunner

[57] ABSTRACT

A thiazole derivative of the general formula:

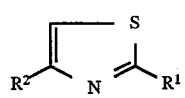

The thiazole derivatives have an excellent inhibitory activity for superoxide radical.

11 Claims, No Drawings

THIAZOLE DERIVATIVES

This application is a continuation of application Ser. No. 08/182,001, filed as PCT/JP93/00700, May 26, 1993, published as Wo93/24472, Dec. 9, 1993, now abandoned.

TECHNICAL FIELD

The present invention relates to thiazole derivatives having an inhibitory activity for the release of superoxide radical.

BACKGROUND ART

It is thought that neutrophilic leukocytes show a germicidal activity to foreign invaders in living bodies by a wondering reaction, a phagocytic activity, generation of superoxide radical ($O_2^-$) and release of lysosomal enzyme and play an important role in protection of living body. While neutrophilic leukocytes have the above reaction for living body protection, it has been made clear that the superoxide radical released by tissues or neutrophilic leukocytes during ischemia of tissues and subsequent blood reperfusion or during acute inflammation at early stage destroys cells, causing functional disturbances of tissues [B. R. Lucchesi: Annual Review of Pharmacology and Toxicology, Vol. 26, p. 201 (1986); B. A. Freeman et al.: Laboratory Investigation, Vol. 47, p. 412 (1982); E. Braunwald, R. A. Kloner: Journal of Clinical Investigation, Vol. 76, p. 1713 (1985); J. L. Romson et al.: Circulation, Vol. 67, p. 1016 (1983)].

It is described in Japanese Patent Publication No. 15935/1971 that compounds represented by the following general formula:

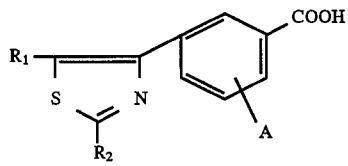

(wherein, $R^1$ is a group selected from the group consisting of a hydrogen atom and a straight-chain or branched-chain lower alkyl group of 1–5 carbon atoms; $R^2$ is a group selected from the group consisting of a lower alkyl group of 1–5 carbon atoms, a phenylalkyl group which may be substituted with a lower alkyl or lower alkoxy group of 1–5 carbon atoms or with one or more halogen atoms, and a phenyl group; A is a group selected from the group consisting of a hydrogen atom, a halogen atom, a hydroxyl group and a lower alkyl or lower alkoxy group of 1–5 carbon atoms), which have similar chemical structures to those of the thiazole derivatives of the present invention, have properties which are advantageous for fibrinolysis, platelet stickiness, ulcers and immunological treatments and can be used for prevention and treatment of thrombosis, arteriosclerosis, gastric ulcer and hypersecretion.

DISCLOSURE OF THE INVENTION

Based on the thought that the major cause for the above-mentioned disturbances in cells, in particular, the disturbances after ischemia and reperfusion in heart, brain, kidney, lung and digestive tract lies in the superoxide radical released by neutrophilic leukocytes, the object of the present invention is to provide a new drug for inhibiting the release of the superoxide radical.

The present inventors made study for the above object and, as a result, found that certain thiazole derivatives show a very strong inhibitory activity for release of superoxide radical in living bodies. Further studies have been made based on the finding, and has led to the completion of the present invention.

The thiazole derivatives of the present invention are novel compounds not described in any literature and are represented by the following general formula (1):

[wherein, $R^1$ represents a phenyl group which may have 1–3 lower alkoxy groups as substituent(s) on the phenyl ring; $R^2$ represents a pyridylcarbonyl group which may have lower alkoxycarbonyl group(s) or carboxyl group(s) as substituent(s), a 5- to 15-membered monocyclic, bicyclic or tricyclic heterocyclic ring residue having 1–3 nitrogen, oxygen or sulfur atoms, or a group of the formula:

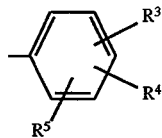

(wherein, $R^3$ represents a carboxyl group, a lower alkoxycarbonyl group, a hydroxyl group-substituted lower alkyl group, a lower alkoxy group, a tri-lower alkyl-substituted silyloxy group, a hydroxyl group or a hydrogen atom; $R^4$ represents a hydrogen atom, a lower alkenyl group or a lower alkyl group; $R^5$ represents an amino-lower alkoxycarbonyl group which may have lower alkyl group(s) as substituent(s), an amino-lower alkoxy-substituted lower alkyl group which may have lower alkyl group(s) as substituent(s), an amino-lower alkoxy group which may have lower alkyl group(s) as substituent(s), a lower alkoxy group having tetrahydropyranyloxy group(s) or hydroxyl group(s), a phenylsulfonyloxy group-substituted lower alkoxy group which may have lower alkyl group(s) as substituent(s) on the phenyl ring, a hydroxysulfonyl group, an amino-lower alkanoyloxy-substituted lower alkyl group which may have lower alkyl group(s) as substituent(s), a lower alkynyloxy group, a group of the formula: —(CO)l—NHR$^6$ (wherein, l represents 0 or 1; and $R^6$ represents a hydroxyl group, a phenyl-lower alkyl group, a carboxyl group-substituted lower alkyl group, an amino group, an aminothiocarbonyl group which may have benzoyl group(s), an amidino group, a group of the formula:

(wherein, $R^7$ represents a lower alkylthio group or a morpholino-lower alkylamino group), a hydrogen atom or a phenyl-lower alkoxycarbonyl group-substituted lower alkyl group), an amino-substituted lower alkanoyloxy-lower alkyl group which may have lower alkyl group(s) as substituent(s), an aminothiocarbonyl group, a group of the formula:

(wherein, $R^8$ represents a hydroxyimino group, a lower alkylthio group, a hydrazino group, a lower alkoxy group, a piperazinyl group which may have lower alkyl group(s), a morpholino group or a morpholino-lower alkylamino group), a 1,2,3,4-tetrazolyl group or a 1,3,4-oxadiazolyl group which may have oxo group(s)); said monocyclic, bicyclic or tricyclic heterocyclic ring residue may have, as substituent(s), 1–3 groups selected from the group consisting of a lower alkyl group, an oxiranyl group, a hydroxyl group-substituted lower alkyl group, a lower alkanoyl group, a lower alkanoyloxy-lower alkyl group, a cyano group, an oxo group, a carboxy-substituted lower alkyl group, a lower alkyl group each having lower alkoxycarbonyl group(s) or cyano group(s) as substituent(s), lower alkoxycarbonyl groups, lower alkyl groups each having, as substituent(s), 1–2 groups selected from the group consisting of a pyridyl group, a furyl group, a phenyl group, a carboxyl group and hydroxyl group, a carboxy-substituted lower alkoxy group, a carboxy-substituted lower alkylthio group, a carboxyl group, a halogen atom, a lower alkoxy group, a hydroxyl group, a group of the formula: —(A)l—$NR^9R^{10}$ (wherein, A represents a lower alkylene group which may have hydroxyl group(s) as substituent(s), or a group of —CO; l is the same as defined above; $R^9$ and $R^{10}$, which may be the same or different, each represent a hydrogen atom, a lower alkyl group, a hydroxyl group, a pyrrolidinyl-lower alkyl group, a carboxy-substituted lower alkyl group or an amino-substituted lower alkyl group which may have lower alkyl group(s) or phenyl-lower alkoxycarbonyl group(s) as substituent(s); $R^9$ and $R^{10}$ may bond to each other directly or via a nitrogen atom or an oxygen atom to form, together with the nitrogen atom to which they bond, a 5- to 6-membered saturated or unsaturated heterocyclic ring; said heterocylic ring may have lower alkyl group(s) or carboxyl group(s) as substituent(s)), amidino groups, aminothiocarbonyl groups and groups of the formula:

(wherein, $R^{8a}$ represents a hydroxyamino group or a lower alkylthio group)].

The thiazole derivatives of the present invention represented by the above general formula (1) have an activity of inhibiting the release of superoxide radical from neutrophilic leukocytes or of removing the superoxide radical. Accordingly, they have an action of preventing or lowering the in vivo production of peroxidized lipids. Hence, the compounds of the present invention are useful as an agent for preventing and treating various disturbances and diseases caused by excessive generation of superoxide radical, in vivo accumulation of peroxidized lipids, or defect of protective organizations therefor. More specifically, the compounds of the present invention are useful in a pharmaceutical field as a drug for protecting various tissue cells from disturbances associated with ischemia and blood reperfusion, for example, a remedy for ulcers of the digestive tract (e.g. stress ulcer), a remedy for ischemia heart disease (e.g. myocardial infarction, arrhythmia), a remedy for cerebrovascular diseases (e.g. cerebral hemorrhage, cerebral infarction, transient cerebral ischemic attack), and a hepatic and renal function improver for disturbances caused by transplant, microcirculation failure, etc., or as a drug for inhibiting various cell function disturbances believed to be caused by the superoxide radical abnormally generated by factors other than ischemia, for example, a remedy for Behcet's syndrome, dermatovascular inflammation, ulcerative colitis, malignant rheumatoid, arthritis, arteriosclerosis, diabetes mellitus, etc.

Each one of the substituents used in the present specification are described specifically as below.

The phenyl group which may have 1–3 lower alkoxy groups as substituent(s) on the phenyl ring, can be exemplified by phenyl groups which may each have 1–3 straight-chain or branched-chain alkoxy groups of 1–6 carbon atoms as substituent(s) on the phenyl ring, such as phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3-propoxy-4-methoxyphenyl, 3,5-dimethoxyphenyl, 3,4-dipentyloxyphenyl, 3,4,5-trimethoxyphenyl, 3-methoxy-4-ethoxyphenyl and the like.

The pyridylcarbonyl group which may have lower alkoxycarbonyl group(s) or carboxyl group(s) as substituent (s), can be exemplified by pyridylcarbonyl groups which may each have straight-chain or branched-chain alkoxycarbonyl group(s) of 1–6 carbon atoms or carboxyl groups as substituent(s), such as pyridylcarbonyl, 6-carboxy-2-pyridylcarbonyl, 3-carboxy-2-pyridylcarbonyl, 4-carboxy-2-pyridylcarbonyl, 5-carboxy-3-pyridylcarbonyl, 2-carboxy-4-pyridylcarbonyl, 6-methoxycarbonyl-2-pyridylcarbonyl, 3-ethoxycarbonyl-2-pyridylcarbonyl, 4-propoxycarbonyl-2-pyridylcarbonyl, 5-butoxycarbonyl-3-pyridylcarbonyl, 2-hexyloxycarbonyl-4-pyridylcarbonyl and the like.

The 5- to 15-membered monocyclic, bicyclic or tricyclic heterocyclic residue having 1–3 nitrogen atoms, 1–3 oxygen atoms or 1–3 sulfur atoms can be exemplified by pyrrolidinyl, piperidinyl, piperazinyl, morpholino, pyridyl, 1,2,5,6-tetrahydropyridyl, thienyl, quinolyl, 1,4-dihydroquinolyl, benzothiazolyl, pyrazyl, pyrimidyl, pyridazyl, pyrrolyl, carbostyril, 3,4-dihydrocarbostyril, 1,2, 3,4-tetrahydroquinolyl, indolyl, isoindolyl, indolinyl, benzoimidazolyl, benzoxazolyl, imidazolidinyl, isoquinolyl, quinazolidinyl, quinoxalinyl, cinnolinyl, phthalazinyl, carbazolyl, acridinyl, chromanyl, isoindolinyl, isochromanyl, pyrazolyl, imidazolyl, pyrazolidinyl, phenothiazinyl, benzofuryl, 2,3-dihydrobenzo[b]furyl, benzothienyl, phenoxathiazinyl, phenoxazinyl, 4H-chromenyl, 1H-indazolyl, phenazinyl, xanthenyl, thianthrenyl, isoindolinyl, 2-imidazolinyl, 2-pyrrolinyl, furyl, oxazolyl, isoxazolyl, thiazolyl, isothiazolyl, pyranyl, pyrazolidinyl, 2-pyrazolinyl, quinucridinyl, 1,4-benzoxazinyl, 3,4-dihydro-2H-1,4-benzoxazinyl, 3,4-dihydro-2H-1,4-benzothiazinyl, 1,4-benzothiazinyl, 1,2,3,4-tetrahydroquinoxalinyl, 1,3-dithia-2,4-dihydronaphthalenyl, phenanthridinyl, 1,4-dithianaphthalenyl, dibenz[b,e] azepinyl, 6,11-dihydro-5H-dibenz[b,e]azepinyl, 4H-furo[2, 3-e]-1,2-oxazinyl or 4a,7a-dihydro-4H-furo[2,3-e]-1,2-oxazinyl.

The lower alkoxycarbonyl group can be exemplified by straight-chain or branched-chain alkoxycarbonyl groups of 1–6 carbon atoms, such as methoxycarbonyl, ethoxycarbonyl, propoxycarbonyl, isopropoxycarbonyl, butoxycarbonyl, tert-butoxycarbonyl, pentyloxycarbonyl, hexyloxycarbonyl and the like.

The hydroxyl group-substituted lower alkyl group can be exemplified by straight-chain or branched-chain alkyl groups of 1–6 carbon atoms each having 1–3 hydroxyl groups, such as hydroxymethyl, 2-hydroxyethyl, 1-hydroxyethyl, 1,2-dihydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl and the like.

The lower alkoxy group can be exemplified by straight-chain or branched-chain alkoxy groups of 1–6 carbon atoms, such as methoxy, ethoxy, propoxy, isopropoxy, butoxy, tert-butoxy, pentyloxy, hexyloxy and the like.

The tri-lower alkyl group-substituted silyloxy group can be exemplified by silyloxy groups each substituted with three straight-chain or branched-chain alkyl groups of 1–6 carbon atoms, such as trimethylsilyloxy, triethylsilyloxy, triisopropylsilyloxy, tributylsilyloxy, tri-tert-butylsilyloxy, tripentylsilyloxy, trihexylsilyloxy, dimethyl-tert-butylsilyloxy and the like.

The lower alkenyl group can be exemplified by straight-chain or branched-chain alkenyl groups of 2–6 carbon atoms, such as vinyl, allyl, 2-butenyl, 3-butenyl, 1-methylallyl, 2-pentenyl, 2-hexenyl and the like.

The lower alkyl group can be exemplified by straight-chain or branched-chain alkyl groups of 1–6 carbon atoms, such as methyl, ethyl, propyl, isopropyl, butyl, tert-butyl, pentyl, hexyl and the like.

The amino-lower alkoxycarbonyl group which may have lower alkyl group(s) as substituent(s), can be exemplified by straight-chain or branched-chain alkoxycarbonyl groups of 1–6 carbon atoms each having an amino group which may have one to two straight-chain or branched-chain alkyl groups of 1–6 carbon atoms as substituent(s), such as aminomethoxycarbonyl, 2-aminoethoxycarbonyl, 1-aminoethoxycarbonyl, 3-aminopropoxycarbonyl, 4-aminobutoxycarbonyl, 5-aminopentyloxycarbonyl, 6-aminohexyloxycarbonyl, 1,1-dimethyl-2-aminoethoxycarbonyl, 2-methyl-3-aminopropoxycarbonyl, methylaminomethoxycarbonyl, 1-ethylaminoethoxycarbonyl, 2-propylaminoethoxycarbonyl, 3-isopropylaminopropoxycarbonyl, 4-butylaminobutoxycarbonyl, 5-pentylaminopentyloxycarbonyl, 6-hexylaminohexyloxycarbonyl, dimethylaminomethoxycarbonyl, 2-dimethylaminoethoxycarbonyl, 3-dimethylaminopropoxycarobnyl, (N-ethyl-N-propylamino)methoxycarbonyl, 2-(N-methyl-N-hexylamino)ethoxycarbonyl and the like.

The amino-lower alkoxy-substituted lower alkyl group which may have lower alkyl group(s) as substituent(s), can be exemplified by straight-chain or branched-chain alkyl groups of 1–6 carbon atoms each having a straight-chain or branched-chain alkoxy group of 1–6 carbon atoms having an amino group which may have one to two straight-chain or branched-chain alkyl groups of 1–6 carbon atoms as substituent(s), such as aminomethoxymethyl, 2-(2-aminoethoxy)ethyl, 1-(1-aminoethoxy)ethyl, 3-(3-aminopropoxy)propyl, 4-(4-aminobutoxy)butyl, 5-(5-aminopentyloxy)pentyl, 6-(6-aminohexyloxy)hexyl, 1,1-dimethyl-2-(1,1-dimethyl-2-aminoethoxy)ethyl, 2-methyl-3-(2-methyl-3-aminopropoxy)propyl, methylaminomethoxymethyl 2-(1-ethylaminoethoxy)ethyl, 1-(2-propylaminoethoxy)ethyl, 3-(3-isopropylaminopropoxy)propyl, 4-(4-butylaminobutoxy)butyl, 5-(5-pentylaminopentyloxy)pentyl, 6-(6-hexylaminohexyloxy)hexyl, dimethylaminomethoxymethyl, 2-dimethylaminoethoxymethyl, 2-(3-dimethylaminopropoxy)ethyl, 4-[(N-ethyl-N-propylamino)methoxy]butyl, 2-[2-(N-methyl-N-hexylamino)ethoxy]ethyl and the like.

The amino-lower alkoxy group which may have lower alkyl group(s) as substituent(s), can be exemplified by straight-chain or branched-chain alkoxy groups of 1–6 carbon atoms each having an amino group which may have one to two straight-chain or branched-chain alkyl groups of 1–6 carbon atoms as substituent(s), such as aminomethoxy, 2-aminoethoxy, 1-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, methylaminomethoxy, 1-ethylaminoethoxy, 2-propylaminoethoxy, 3-isopropylaminopropoxy, 4-butylaminobutoxy, 5-pentylaminopentyloxy, 6-hexylaminohexyloxy, dimethylaminomethoxy, 2-dimethylaminoethoxy, 3-dimethylaminopropoxy, (N-ethyl-N-propylamino)methoxy, 2-(N-methyl-N-hexylamino)ethoxy and the like.

The lower alkoxy group having tetrahydropyranyloxy group(s) or hydroxyl group(s) can be exemplified by lower alkyl groups each having 1–3 tetrahydropyranyloxy group (s) or hydroxyl group(s), such as 2-(2-tetrahydropyranyloxy)ethoxy, (3-tetrahydropyranyloxy)methoxy, 1-(4-tetrahydropyranyloxy)ethoxy, 3-(2-tetrahydropyranyloxy)propoxy, 4-(3-tetrahydropyranyloxy)butoxy, 5-(2-tetrahydropyranyloxy)pentyloxy, 6-(3-tetrahydropyranyloxy)hexyloxy, hydroxymethoxy, 2-hydroxyethoxy, 1-hydroxyethoxy, 3-hydroxypropoxy, 2,3-dihydroxypropoxy, 4-hydroxybutoxy, 1,1-dimethyl-2-hydroxyethoxy, 5,5,4-trihydroxypentyloxy, 5-hydroxypentyloxy, 6-hydroxyhexyloxy, 1-hydroxyisopropoxy, 2-methyl-3-hydroxypropoxy and the like.

The phenylsulfonyloxy group-substituted lower alkoxy group which may have lower alkyl group(s) as substituent(s) on the phenyl ring, can be exemplified by straight-chain or branched-chain alkoxy groups of 1–6 carbon atoms each substituted with a phenylsulfonyloxy group which may have one to three straight-chain or branched-chain alkyl groups of 1–6 carbon atoms as substituent(s) on the phenyl ring, such as (2-methylphenylsulfonyloxy)methoxy, 1-(3-methylphenylsulfonyloxy)ethoxy, 2-(4-methylphenylsulfonyloxy)ethoxy, 3-(2-ethylphenylsulfonyloxy)propoxy, 4-(3-ethylphenylsulfonyloxy)butoxy, 5-(4-ethylphenylsulfonyloxy)pentyloxy, 6-(3-butylphenylsulfonyloxy)hexyloxy, 1,1-dimethyl-2-(4-isopropylphenylsulfonyloxy)ethoxy, 2-methyl-3-(4-pentylphenylsulfonyloxy)propoxy, (4-hexylphenylsulfonyloxy)methoxy, 2-(3,4-dimethylphenylsulfonyloxy)ethoxy, (3,4,5-trimethylphenylsulfonyloxy)methoxy and the like.

The amino-lower alkanoyloxy-substituted lower alkyl group which may have lower alkyl group(s) as substituent (s), can be exemplified by straight-chain or branched-chain alkyl groups of 1–6 carbon atoms each having a straight-chain or branched-chain alkanoyloxy group of 2–6 carbon atoms substituted with an amino group which may have one to two straight-chain or branched-chain alkyl groups of 1–6 carbon atoms as substituent(s), such as (2-aminoacetyloxy) methyl, 2-(2-aminoacetyloxy)ethyl, 1-(2-aminoacetyloxy) ethyl, 3-(3-aminopropionyloxy)propyl, 4-(4-aminobutyryloxy)butyl, 5-(5aminopentanoyloxy)pentyl, 6-(6-aminohexanoyloxy)hexyl, 1,1-dimethyl-2-(2- aminoacetyloxy)ethyl, 2-methyl-3-(3-aminopropionyloxy) propyl, (2-methylaminoacetyloxy)methyl, 1-(2-ethylaminoacetyloxy)ethyl, 2-(2-propylaminoacetyloxy) ethyl, 3-(3-isopropylaminopropionyloxy)propyl, 4-(4-butylaminobutyryloxy)butyl, 5-(5-pentylaminopentanoyloxy)pentyl, 6-(6-hexylaminohexanoyloxy)hexyl, 2-dimethylaminoacetyloxy) methyl, [2-(N-ethyl-N-propylamino)acetyloxy]methyl, 2-[2-(N-methyl-N-hexylamino)acetyloxy]ethyl and the like.

The lower alkynyloxy group can be exemplified by straight-chain or branched-chain alkynyloxy groups of 2–6 carbon atoms, such as ethynyloxy, (2-propynyl)oxy, (2-butynyl)oxy, (3-butynyl)oxy, (1-methyl-2-propynyl)oxy, (2-pentynyl)oxy, (2-hexynyl)oxy and the like.

As to the phenyl-lower alkyl group, there can be mentioned phenylalkyl groups whose alkyl moiety is a straight-chain or branched-chain alkyl group of 1–6 carbon atoms, such as benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl and the like.

As to the carboxy-substituted lower alkyl group, there can be mentioned carboxyalkyl groups whose alkyl moiety is a straight-chain or branched-chain alkyl group of 1–6 carbon atoms, such as carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, 2-methyl-3-carboxypropyl and the like.

The aminothiocarbonyl group which may have benzoyl group(s), can be exemplified by aminothiocarbonyl and benzoylaminothiocarbonyl.

The piperazinyl group which may have lower alkyl group (s), can be exemplified by piperazinyl groups which may have one to three straight-chain or branched-chain alkyl groups of 1–6 carbon atoms, such as 1-piperazinyl, 4-methyl-1-piperazinyl, 4-ethyl-1-piperazinyl, 3-propyl-1-piperazinyl, 2-butyl-1-piperazinyl, 4-hexyl-2-piperazinyl, 4-pentyl-3-piperazinyl, 3,4-dimethyl-1-piperazinyl, 3,4,5-trimethyl-1-piperazinyl and the like.

The phenyl-lower alkoxycarbonyl group-substituted lower alkyl group can be exemplified by straight-chain or branched-chain alkyl groups of 1–6 carbon atoms each having a phenylalkoxycarbonyl group whose alkoxy moiety is a straight-chain or branched-chain alkoxy group of 1–6 carbon atoms, such as benzyloxycarbonylmethyl, 2-(2-phenylethoxycarbonyl)ethyl, 1-(1-phenylethoxycarbonyl) ethyl, 3-(3-phenylpropoxycarbonyl)propyl, 4-(4-phenylbutoxycarbonyl)butyl, 1,1-dimethyl-2-(1,1-dimethyl-2-phenylethoxycarbonyl)ethyl, 5-(5-phenylpentyloxycarbonyl)pentyl, 6-(6-phenylhexyloxycarbonyl)hexyl, 2-methyl-2-(2-methyl-3-phenylpropoxycarbonyl)ethyl and the like.

The amino-substituted lower alkanoyloxy-lower alkyl group which may have lower alkyl group(s) as substitutent (s), can be exemplified by straight-chain or branched-chain alkyl groups of 1–6 carbon atoms each substituted with a straight-chain or branched-chain alkanoyloxy group of 2–6 carbon atoms having an amino group which may have one to two straight-chain or branched-chain alkyl group of 1–6 carbon atoms, such as (2-aminoacetyloxy)methyl, 1-(2-aminopropionyloxy)ethyl, 2-(3-aminopropionyloxy)ethyl, 3-(4-aminobutyryloxy)propyl, 4-(5-aminopentanoyloxy) butyl, 5-(6-aminohexanoyloxy)pentyl, 6-(1,1-dimethyl-2-aminoacetyloxy)hexyl, 3-(2-methyl-3-aminopropionyloxy) propyl, methylaminoacetyloxymethyl, dimethylaminoacetyloxymethyl, 2-(2-ethylaminopropionyloxy)ethyl, 3-(3-propylaminopropionyloxy)propyl, 4-(4-isopropylaminobutyryloxy)butyl, 5-(5-butylaminopentanoyloxy)pentyl, 6-(6-pentylaminohexanoyloxy)hexyl, (2-hexylaminoacetyloxy) methyl, [2-(N-ethyl-N-propylamino)acetyloxy]methyl, 2-[3-(N-methyl-N-hexylamino)propionylox]ethyl and the like.

The lower alkylthio group can be exemplified by straight-chain or branched-chain alkylthio groups of 1–6 carbon atoms, such as methylthio, ethylthio, propylthio, isopropylthio, butylthio, tert-butylthio, pentylthio, hexylthio and the like.

As to the morpholino-lower alkylamino group, there can be mentioned morpholinoalkylamino groups whose alkyl moiety is a straight-chain or branched-chain alkyl group of 1–6 carbon atoms, such as morpholinomethylamino, 2-morpholinoethylamino, 1-morpholinoethylamino, 3-morpholinopropylamino, 4-morpholinobutylamino, 5-(2-morpholino)pentylamino, 6-(3-morpholino)hexylamino, 1,1-dimethyl-2-(4-morpholino)ethylamino, 2-methyl-3-morpholinopropylamino and the like.

The 1,3,4-oxadiazolyl group which may have oxo group (s), can be exemplified by 1,3,4-oxadiazolyl, 5-oxo-1,3,4-oxazolyl-2-yl and the like.

As to the lower alkanoyl group, there can be mentioned straight-chain or branched-chain alkanoyl groups of 1–6 carbon atoms, such as formyl, acetyl, propionyl, butyryl, isobutyryl, pentanoyl, tert-butylcarbonyl, hexanoyl and the like.

As to the lower alkanoyloxy-substituted lower alkyl group, there can be mentioned straight-chain or branched-chain alkyl groups of 1–6 carbon atoms each having one to three straight-chain or branched-chain alkanoyloxy groups of 1–6 carbon atoms, such as formyloxymethyl, acetyloxymethyl, 2-propionyloxyethyl, 1-butyryloxyethyl, 3-acetyloxypropyl, 2,3-diacetyloxypropyl, 4-isobutyryloxybutyl, 5-pentanoyloxypentyl, 6-tert-butylcarbonyloxyhexyl, 1,1-dimethyl-2-hexanoyloxyethyl, 5,5,4-triacetyloxypentyl, 2-methyl-3-acetyloxypropyl and the like.

As to the carboxy-substituted lower alkoxy group, there can be mentioned carboxyalkoxy groups whose alkoxy moiety is a straight-chain or branched-chain alkoxy group of 1–6 carbon atoms, such as carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy, 2-methyl-3-carboxypropoxy and the like.

The lower alkyl group having lower alkoxycarbonyl group(s) or cyano group(s) as substituent(s) can be exemplified by straight-chain or branched-chain alkyl groups of 1–6 carbon atoms each having, as substituent(s), straight-chain or branched-chain alkoxycarbonyl group(s) of 1–6 carbon atoms or cyano group(s), such as cyanomethyl, 1-cyanoethyl, 2-cyanoethyl, 3-cyanopropyl, 4-cyanobutyl, 1,1-dimethyl-2-cyanoethyl, 5-cyanopentyl, 6-cyanohexyl, 2-methyl-3-cyanopropyl, methoxycarbonylmethyl, ethoxycarbonylmethyl, 2-propoxycarbonylethyl, 1-butoxycarbonylethyl, 3-methoxycarbonylpropyl, 2,3-diethoxycarbonylpropyl, 4-isobutoxycarbonylbutyl, 5-pentyloxycarbonylpentyl, 6-tert-butoxycarbonylhexyl, 1,1-dimethyl-2-hexyloxycarbonylethyl, 5,5,4-trimethoxycarbonylpentyl, 2-methyl-3-ethoxycarbonylpropyl, 1-ethoxycarbonyl-1-cyanomethyl, 2-ethoxycarbonyl-1-cyanoethyl and the like.

The lower alkyl group having, as substituent(s), 1–2 groups selected from the group consisting of pyridyl groups, furyl groups, phenyl groups, carboxyl groups and hydroxyl groups, can be exemplified by straight-chain or branched-chain lower alkyl groups of 1–6 carbon atoms each having, as substituent(s), 1–2 groups selected from the group consisting of pyridyl groups, furyl groups, phenyl groups, carboxyl groups and hydroxyl groups, such as (2-pyridyl) methyl, 1-(3pyridyl)ethyl, 2-(4-pyridyl)ethyl, 3-(2-pyridyl) propyl, 4-(3-pyridyl)butyl, 5-(4-pyridyl)pentyl, 6-(2-pyridyl)hexyl, 1,1-dimethyl-2-(3-pyridyl)ethyl, 2-methyl-3-(4-pyridyl)propyl, 1-(2-pyridyl)-1-hydroxymethyl, 2-(3-pyridyl)-1-hydroxyethyl, 3-(4-pyridyl)-1-hydroxypropyl, 5-(2-pyridyl)-4-hydroxypentyl, 6-(2-pyridyl)-6-hydroxyhexyl, (2-furyl)methyl, 1-(3-furyl)ethyl, 2-(2-furyl)ethyl, 3-(2-furyl)propyl, 4-(3-furyl)butyl, 5-(2-furyl)pentyl, 6-(3-furyl)hexyl, 1,1-dimethyl-2-(2-furyl)ethyl, 2-methyl-3-(2-furyl)propyl, 1-(2-furyl)-1-hydroxymethyl, 2-(2-furyl)-1-hydroxyethyl, 1,1-diphenylmethyl, benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 1-phenyl-1-hydroxymethyl, 2-phenyl-1-hydroxyethyl, 1-phenyl-2-hydroxyethyl, 3-phenyl-1-hydroxypropyl, 4-phenyl-4-hydroxybutyl, 5-phenyl-5-hydroxypentyl, 6-phenyl-6-hydroxyhexyl, 2-methyl-3-phenyl-3-hydroxypropyl, carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, 2-methyl-3-carboxypropyl, 1-carboxy-1-hydroxymethyl, 2-carboxy-1-hydroxyethyl, 3-carboxy-1-hydroxypropyl, 5-carboxy-4-hydroxypentyl, 6-carboxy-6-hydroxyhexyl and the like.

As to the carboxy-substituted lower alkylthio group, there can be mentioned carboxyalkylthio groups whose alkylthio moiety is a straight-chain or branched-chain alkylthio group of 1–6 carbon atoms, such as carboxymethylthio, 2-carboxyethylthio, 1-carboxyethylthio, 3-carboxypropylthio, 4-carboxybutylthio, 5-carboxypentylthio, 6-carboxyhexylthio, 1,1-dimethyl-2-carboxyethylthio, 2-methyl-3-carboxypropylthio and the like.

As to the halogen atom, there can be mentioned, for example, a fluorine atom, a chlorine atom, a bromine atom and an iodine atom.

As to the pyrrolidinyl-lower alkyl group, there can be mentioned pyrrolidinylalkyl groups whose alkyl moiety is a straight-chain or branched-chain alkyl group of 1–6 carbon atoms, such as (1-pyrrolidinyl)methyl, 2-(1-pyrrolidinyl) ethyl, 1-(1-pyrrolidinyl)ethyl, 3-(1-pyrrolidinyl)propyl, 4-(1-pyrrolidinyl)butyl, 5-(2-pyrrolidinyl)pentyl, 6-(3-pyrrolidinyl)hexyl, 1,1-dimethyl-2-(2-pyrrolidinyl)ethyl, 2-methyl-3-(1-pyrrolidinyl)propyl and the like.

The amino-lower alkyl group which may have lower alkyl group(s) or phenyl-lower alkoxycarbonyl group(s) as substituent(s) can be exemplified by an amino-lower alkyl group wherein the alkyl moiety is a straight-chain or branched-chain alkyl groups having 1–6 carbon atoms, and the amino moiety may have one or two substituents selected from the group consisting of a straight-chain or branched-chain alkyl groups having 1–6 carbon atoms and a phenylalkoxycarbonyl group wherein the alkoxycarbonyl moiety is a straight-chain or branched chain alkoxycarbonyl group having 1–6 carbon atoms, such as aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, (N-ethyl-N-propylamino)methyl, 2-(N-methyl-N-hexylamino)ethyl, 2-dimethylaminoethyl, benzyloxycarbonylaminomethyl, 2-benzyloxycarbonylaminoethyl, 1-(2-phenylethoxycarbonylamino)ethyl, 2-(3-phenylpropoxycarbonylamino)ethyl, 3-(4-phenylbutoxycarbonylamino)propyl, 4-(5-phenylpentyloxycarbonylamino)butyl, 5-(6-phenylhexyloxycarbonylamino)pentyl, 6-(benzyloxycarbonylamino)hexyl, dibenzyloxycarbonylaminomethyl, 2-(N-methyl-N-benzyloxycarbonylamino)ethyl and the like.

The 5- to 6-membered saturated or unsaturated heterocyclic ring formed by $R^9$ and $R^{10}$, together with the nitrogen atom to which they bond, when they bond to each other directly or via a nitrogen atom or an oxygen atom, can be exemplified by piperazinyl, pyrrolidinyl, morpholinyl, piperidinyl, pyrrolyl, imidazolyl, pyrazolyl, 2-pyrrolinyl, 2-imidazolinyl, imidazolidinyl, 2-pyrazolinyl, pyrazolidinyl, 1,2,4-triazolyl and 1,2,5,6-tetrahydropyridyl.

The above-mentioned heterocyclic ring substituted with carboxyl group(s) or lower alkyl group(s) can be exemplified by the above-mentioned heterocyclic rings each substituted with carboxyl group(s) or straight-chain or branched-chain alkyl group(s) of 1–6 carbon atoms, such as 3-carboxypiperazinyl, 3-carboxypyrrolidinyl, 2-carboxypyrrolidinyl; 4-carboxypiperidinyl, 3-carboxypiperazinyl, 2-carboxymorpholino, 4-methylpiperazinyl, 4-ethylpiperazinyl, 3-ethylpyrrolidinyl, 2-propylpyrrolidinyl, 4-butylpiperidinyl, 3-pentylmorpholino, 3-methyl-1,2,4-triazolyl, 2-hexylpiperazinyl, 2-carboxypyrrolidinyl and the like.

The above-mentioned heterocyclic ring having 1–3 groups selected from the group consisting of oxo groups, lower alkyl groups, lower alkanoyl groups, lower alkyl groups each having lower alkoxycarbonyl group(s) or cyano group(s) as substituent(s), lower alkanoyloxy-lower alkyl groups, hydroxyl groups, carboxyl groups, lower alkoxycarbonyl groups, carboxy-substituted lower alkyl groups, groups —(A)l—NR$^9$R$^{10}$ (A and l are the same as defined above; $R^9$ and $R^{10}$, which may be the same or different, each represent a hydrogen atom, a lower alkyl group, a hydroxyl group, a pyrrolidinyl-lower alkyl group, a carboxy-substituted lower alkyl group or an amino-substituted lower alkyl group which may have lower alkyl group(s) or phenyl-lower alkoxycarbonyl group(s) as substituent(s); $R^9$ and $R^{10}$ may bond to each other directly or via a nitrogen atom or an oxygen atom to form, together with the nitrogen atom to which they bond, a 5- to 6-membered saturated or unsaturated heterocyclic ring; said heterocylic ring may have lower alkyl group(s) or carboxyl group(s) as substituent(s)), cyano groups, hydroxyl group-substituted lower alkyl groups, lower alkyl groups each having, as substituent(s), 1–2 groups selected from the group consisting of pyridyl groups, furyl groups, phenyl groups, carboxyl groups and hydroxyl groups, carboxy-substituted lower alkoxy groups, carboxy-substituted lower alkylthio groups, halogen atoms, lower alkoxy groups, oxiranyl groups, amidino groups, aminothiocarbonyl groups and groups of the formula:

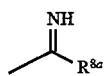

(wherein, $R^{8a}$ represents a hydroxyimino group or a lower alkylthio group), can be exemplified by the above-mentioned heterocyclic rings each having 1–3 groups selected from the group consisting of oxo groups, straight-chain or branched-chain alkyl groups of 1–6 carbon atoms, straight-chain or branched-chain alkanoyl groups of 1–6 carbon atoms, straight-chain or branched-chain alkyl groups of 1–6 carbon atoms each having, as substituent(s), straight-chain or branched-chain alkoxycarbonyl group(s) of 1–6 carbon atoms or cyano group(s), straight-chain or branched-chain alkyl groups of 1–6 carbon atoms each having one to three straight-chain or branched-chain alkanoyloxy groups of 1–6 carbon atoms, hydroxyl groups, carboxyl groups, straight-chain or branched-chain alkoxycarbonyl groups of 1–6 carbon atoms, carboxyalkyl groups whose alkyl moiety is a straight-chain or branched-chain alkyl group of 1–6 carbon atoms, groups of the formula: —(A)l—NR$^9$R$^{10}$ (wherein, A and l are the same as defined above; R$^9$ and R$^{10}$, which may be the same or different, each represent a hydrogen atom, a straight-chain or branched-chain alkyl group of 1–6 carbon atoms, a hydroxyl group, a pyrrolidinylalkyl group whose alkyl moiety is a straight-chain or branched-chain alkyl group of 1–6 carbon atoms, a carboxyalkyl group whose alkyl moiety is a straight-chain or branched-chain alkyl group of 1–6 carbon atoms, or a straight-chain or branched-chain alkyl group of 1–6 carbon atom having an amino group which may have, one or two substituents, selected from the group consisting of a straight-chain or branched-chain alkyl group of 1–6 carbon atoms and a phenylalkoxycarbonyl group wherein the alkoxycarbonyl moiety is a straight-chain or branched-chain alkoxycarbonyl groups of 1–6 carbon atoms; R$^9$ and R$^{10}$ may bond to each other directly or via a nitrogen atom or an oxygen atom to form, together with the nitrogen atom to which they bond, a 5- to 6-membered saturated or unsaturated heterocyclic ring; said heterocylic ring may have straight-chain or branched-chain alkyl group(s) of 1–6 carbon atoms or carboxyl group(s) as substituent(s)), cyano groups, straight-chain or branched-chain alkyl groups of 1–6 carbon atoms each having 1–3 hydroxyl groups, straight-chain or branched-chain alkyl groups each having, as substituent(s), 1–2 groups selected from the group consisting of pyridyl groups, furyl groups, phenyl groups, carboxyl groups and hydroxyl groups, carboxyalkoxy groups whose alkoxy moiety is a straight-chain or branched-chain alkoxy group of 1–6 carbon atoms, carboxyalkylthio groups whose alkylthio moiety is a straight-chain or branched-chain alkylthio group of 1–6 carbon atoms, halogen atoms, straight-chain or branched-chain alkoxy groups of 1–6 carbon atoms, oxiranyl groups, amidino groups, aminothiocarbonyl groups and groups of the formula:

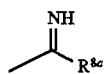

(wherein, R$^{8a}$ represents a hydroxyimino group or a straight-chain or branched-chain alkylthio group of 1–6 carbon atoms). Specific examples of these heterocyclic rings are dibenz[b,e]azepin-3-yl-6-one, 4-oxo-1,4-dihydroquinolyl, 1-oxopyridyl, 2-oxopyridyl, 1-methyl-3,4-dihydrocarbostyril, 1-ethylcarbostyril, 1-butyl-3,4-dihydrocarbostyril, 1-hexylcarbostyril, 6-methoxy-3,4-dihydrocarbostyril, 3-oxo-4-methyl-3,4-dihydro-2H-1,4-benzothiazinyl, 3-oxo-3,4-dihydro-2H-1,4-benzothiazinyl, 2-carboxy-3-hydroxypyridyl, 2-acetyloxymethylpyridyl, 1-ethoxypyridyl, 2-ethoxycarbonyl-3-hydroxypyridyl, 3-ethoxycarbonyl-4a,7a-dihydro-4H-furo[2,3-e]-1,2-oxazinyl, 2-chloropyridyl, 4-chloropyridyl, 2-[1-(2-pyridyl)-1-hydroxymethyl]pyridyl, 2-[1-(2-furyl)-1-hydroxymethyl]pyridyl, 2-(1-phenyl-1-hydroxymethyl)pyridyl, 4-methyl-1, 2,3,4-tetrahydroquinoxalinyl, 2-carboxymethylpyridyl, 2-(2-carboxyethyl)pyridyl, 2-cyanomethylpyridyl, 2-(4-methyl-1-piperazinyl)pyridyl, 2-morpholinopyridyl, 2-(1,2,4-triazol-1-yl)pyridyl, 2-(2-carboxy-1-pyrrolidinyl)pyridyl, 2-(2-carboxyethyl)aminopyridyl, 2-(2-dimethylaminoethyl)aminopyridyl, 2-(2-carboxyethoxy)pyridyl, 2-(2-carboxyethylthio)pyridyl, 2-carboxypyrazyl, 4-carboxypyrimidyl, 5-carboxyimidazolyl, 1-methyl-1,2,3,4-tetrahydroquinolyl, 7-hydroxy-3,4-dihydrocarbostyril, 8-hydroxy-3,4-dihydrocarbostyril, 3-fluoro-2-carboxypyridyl, 4-methoxy-2-carboxypyridyl, 3-oxo-3,4-dihydro-2H-1,4-benzoxazinyl, 3-hydroxy-2-carboxypyridyl, 2-oxobenzimidazolyl, 4-methyl-3,4-dihydro-2H-1,4-benzoxazinyl, 4-amino-2-carboxypyridyl, 2-oxobenzothiazolyl, 2-oxobenzoxazolyl, 2-oxo-3-methylbenzothiazolyl, 1,3-dimethyl-2-oxobenzimidazolyl, 6-hydroxy-3,4-dimethylquinolyl, 4-oxopyridyl, 1-propyl-1,2,3,4-tetrahydroquinolyl, 4-pentyl-1,2,3,4-tetrahydroquinoxalyl, 3-dimethylamino-2-carboxypyridyl, 2,4-dicarboxypyridyl, 2-carboxypyridyl, 2-carboxypyrrolyl, 2-ethoxycarbonylpyridyl, 2-methoxycarbonylpyrrolyl, 1-methylpyridium, 1-methyl-1,2,5,6-tetrahydropyridyl, 2-methoxycarbonylfuryl, 2-carboxyfuryl, 2-dimethylaminocarbonylpyridyl, 1-oxo-2-hydroxymethyl-4-methylpyridyl, 2-hydroxymethylpyridyl, 2-ethoxycarbonyl-4-methylpyridyl, 2-carboxy-4-methylpyridyl, 2-(4-methyl-1-piperazinyl)carbonylpyridyl, 2-(2-dimethylaminoethoxycarbonyl)pyridyl, 2-dimethylaminomethylpyridyl, 2-ethoxycarbonylthienyl, 2-methyl-7-carboxybenzofuryl, 2-carboxythienyl, 4-ethoxycarbonylthiazolyl, 4-carboxythiazolyl, 4-methyl-5-carboxythiazolyl, 3-carboxypyridyl, 2,2-dimethyl-7-carboxy-2,3-dihydrobenzo-[b]furyl, 4-carboxypyridyl, 2-cyanopyridyl, 4-cyanopyridyl, 2-methyl-4-carbamoylpyridyl, 2,6-dimethyl-3-carbamoylpyridyl, 2-methyl-3-carboxypyridyl, 2,6-dimethyl-3-carboxypyridyl, 2-formylpyridyl, 3-acetylpyridyl, 2-{[2-(1-pyrrolidinyl)ethyl]aminocarbonyl}pyridyl, 2-aminothiocarbonylpyridyl, 2-(1-imino-1-methylthiomethyl)pyridyl, 2-amidinopyridyl, 2-(2-dimethylaminoethylamino)pyridyl, 2-(1,2,3,4-tetrazol-5-yl)pyridyl, 2-(2-carboxy-1-pyrrolidinyl)pyridyl, 3-carboxypyrazinyl, 4-(4-methyl-1-piperazinyl)pyridyl, 2-[2-(4-methyl-1-piperazinyl)-1-hydroxyethyl]pyridyl, 2-(2-dimethylamino-1-hydroxyethyl)pyridyl, 2-(2-hydroxy-1-dimethylaminoethyl)pyridyl, 2-(1-carboxy-1-hydroxymethyl)pyridyl, 2-[(2-benzyloxycarbonylaminoethyl)aminocarbonyl]pyridyl, 2-(1-hydroxyamino-liminomethyl)pyridyl, 4-oxopyrazinyl, 1,4-dioxopyrazinyl, 3-cyanopyrazinyl, 5-cyanopyrazinyl, 2-(1-ethoxycabonyl-1cyanomethyl)pyridyl, 2-(1,2-dihydroxyethyl)pyridyl, 6-carboxypyrimidinyl, 2-oxiranylpyridyl, 1-oxopyrimidinyl, 6-cyanopyrimidinyl, 1-oxopyridyl, 2-cyanopyridyl and 2-(1-methoxycarbonyl-1-cyanomethyl)pyridyl.

The lower alkylene group which may have hydroxyl group(s) as substituent(s), can be exemplified by straight-chain or branched-chain alkylene groups of 1–6 carbon atoms which may each have hydroxyl group(s) as substituent(s), such as methylene, ethylene, trimethylene, tetramethylene, pentamethylene, hexamethylene, 2-methyltrimethylene, 2,2-dimethyltrimethylene, 1-methyltrimethylene, methylmethylene, ethylmethylene, 1-hydroxyethylene, 2-hydroxyethylene, 2-hydroxytrimethylene, 2-hydroxytetramethylene, 3-hydroxypentamethylene, 3-hydroxyhexamehtylene and the like.

The present compounds of general formula (1) can be produced, for example, by the following processes.

[Reaction formula 1]

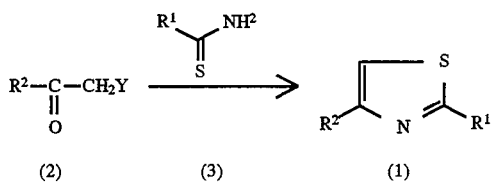

(wherein, $R^1$ and $R^2$ are the same as defined above, and Y represents a halogen atom.)

The reaction of a compound (2) with a compound (3) can be conducted in an appropriate solvent with heating. The solvent can be exemplified by alcohols such as methanol, ethanol, propanol, butanol, 3-methoxy-1-butanol, ethyl cellosolve, methyl cellosolve and the like; aromatic hydrocarbons such as benzene, toluene, xylene, o-dichlorobenzene and the like; ethers such as diethyl ether, tetrahydrofuran, dioxane, diglyme, monoglyme and the like; halogenated hydrocarbons such as dichloromethane, chloroform, carbon tetrachloride and the like; polar solvents such as dimethylformamide, dimethyl sulfoxide, hexamethylphosphoric triamide, acetonitrile and the like; and mixtures thereof. The reaction is conducted generally at room temperature to 150° C., preferably at room temperature to about 100° C. and is complete in about 1–15 hours. The amount of the compound (3) used is at least one mole, preferably one to about 1.5 moles per mole of the compound (2).

[Reaction formula 2]

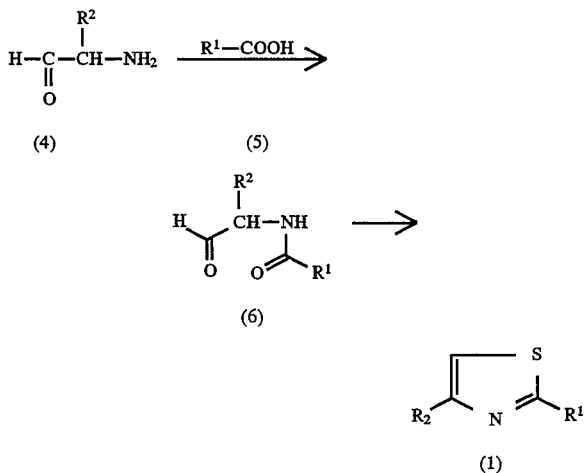

(wherein, $R^1$ and $R^2$ are the same as defined above.)

The reaction of a compound (4) with a compound (5) can be achieved by subjecting them to an ordinary amido-bond formation reaction. In this case, the carboxylic acid (5) may have been activated.

In the amido-bond formation, the conditions used in ordinary amido-bond formation reactions can be applied. There can be mentioned, for example, (a) a mixed acid anhydride process, i.e. a process which comprises reacting a carboxylic acid (5) with an alkylhalocarboxylic acid to form a mixed acid anhydride and reacting the anhydride with a compound (4); (b) an active ester or active amide process, i.e. a process which comprises converting a carboxylic acid (5) into an active ester such as p-nitrohenylester, N-hydroxysuccinimide ester, 1-hydroxybenzotriazole ester or the like or an active amide with benzoxazolin-2-thione and reacting the active ester or the active amide with a compound (4); (c) a carbodiimide process, i.e. a process which comprises combining a carboxylic acid (5) with a compound (4) in the presence of a dehydrating agent such as dicyclohexylcarbodiimide, carbonyldiimidazole or the like; (d) a carboxylic acid halide process, i.e. a process which comprises converting a carboxylic acid (5) into a halide and reacting the halide with a compound (4); (e) other processes, for example, a process which comprises converting a carboxylic acid (5) into a carboxylic acid anhydride by the use of a dehydrating agent such as acetic anhydride or the like and then reacting the carboxylic acid anhydride with a compound (4) and a process which comprises converting a carboxylic acid (5) into an ester with, for example, a lower alcohol and then reacting the ester with a compound (4) at a high pressure at a high temperature. There can also be used a process which comprises activating a carboxylic acid (5) with a phosphorus compound such as triphenylphosphine, diethyl chlorophosphate or the like, followed by reaction with a compound (5).

The alkylhalocarboxylic acid used in the mixed acid anhydride process includes, for example, methyl chloroformate, methyl bromoformate, ethyl chloroformate, ethyl bromoformate and isobutyl chloroformate. The mixed acid anhydride can be obtained by an ordinary Schotten-Baumann reaction and, generally without being isolated, it is reacted with a compound (4), whereby a compound can be produced. The Schotten-Baumann reaction is conducted generally in the presence of a basic compound. The basic compound can be any basic compound commonly used in the Schotten-baumann reaction and includes, for example, organic bases such as triethylamine, trimethylamine, pyridine, dimethylaniline, N-methylmorpholine, 4-dimethylaminopyridine, DBN, DBU, DABCO and the like; and inorganic bases such as potassium carbonate, sodium carbonate, potassium hydrogencarbonate, sodium hydrogencarbonate and the like. The reaction is conducted at about −20° C. to 100° C., preferably at 0°–50° C. and the reaction time is about 5 minutes to 10 hours, preferably 5 minutes to 2 hours. The reaction of the obtained mixed acid anhydride with a compound (4) is conducted at about −20° C. to 150° C., preferably at 10°–50° C. for about 5 minutes to 10 hours, preferably about 5 minutes to 5 hours. In the mixed acid anhydride process, use of solvent is not essential but the process is conducted generally in a solvent. The solvent can be any solvent commonly used in the mixed acid anhydride process. Specific examples thereof are halogenated hydrocarbons such as methylene chloride, chloroform, dichloroethane and the like; aromatic hydrocarbons such as benzene, toluene, xylene and the like; ethers such as diethyl ether, diisopropyl ether, tetrahydrofuran, dimethoxyethane and the like; esters such as methyl acetate, ethyl acetate and the like; aprotic polar solvents such as dimethylformamide, dimethyl sulfoxide, hexamethylphosphoric triamide and the like. The proportions of the carboxylic acid(5), alkylhalocarboxylic acid and compound (4) used in the process are generally at least equimolar but, preferably, the alkylhalocarboxylic acid and compound (4) are used each in an amount of 1–2 moles per mole of the carboxylic acid (5).

The active ester or active amide process (b), when, for example, benzoxazoline-2-thionamide is used, is conducted by reacting said amide at 0°–150° C., preferably at 10°–100° C. for 0.5–75 hours using an appropriate solvent not adversely affecting the reaction, such as the same solvent as used in the mixed acid anhydride process, 1-methyl-2-pyrrolidone or the like. In this case, benzoxazoline-2-thionamide is used in an amount of generally at least 1 mole, preferably 1–2 moles per mole of the compound (4). When N-hydroxysuccinimide ester is used, the reaction proceeds favorably by the use of an appropriate basic compound, for example, the same basic compound as used in the carboxylic acid halide process described below.

The carboxylic acid halide process (c) is conducted by reacting a carboxylic acid (5) with a halogenating agent to form a carboxylic acid halide and, after isolating and purifying the halide or without doing it, reacting the halide with a compound (4). The reaction of the carboxylic acid halide with the compound (4) is conducted in an appropriate solvent in the presence or absence of a dehalogenating agent. As the dehalogenating agent, a basic compound is generally used. The basic compound includes the basic compounds used in the Schotten-Baumann reaction, sodium hydroxide, potassium hydroxide, sodium hydride, potassium hydride, silver carbonate, alkali metal alcoholates (e.g. sodium methylate and sodium ethylate), etc. It is possible to use the compound (4) in an excessive amount to allow the compound to act also as a dehalogenating agent. The solvent includes the solvents used in the Schotten-Baumann reaction, water, alcohols (e.g. methanol, ethanol, propanol, butanol, 3-methoxy-1-butanol, ethyl cellosolve and methyl cellosolve), pyridine, acetone, acetonitrile, mixed solvents of two or more thereof, etc. The proportions of the compound (4) and the carboxylic acid halide used are not particularly restricted and can be selected in a wide range, but the latter is used in an amount of generally at least 1 mole, preferably 1-5 moles per mole of the former. The reaction is conducted generally at about −30° C. to 180° C., preferably at about 0°-150° C. and is complete generally in 5 minutes to 30 hours. The carboxylic acid halide is produced by reacting a carboxylic acid (5) with a halogenating agent in the presence or absence of a solvent. The solvent can be any solvent as long as it gives no adverse effect on the reaction, and includes, for example, aromatic hydrocarbons (e.g. benzene, toluene and xylene), halogenated hydrocarbons (e.g. chloroform, methylene chloride and carbon tetrachloride), ethers (e.g. dioxane, tetrahydrofuran and diethyl ether), dimethylformamide and dimethyl sulfoxide. The halogenating agent can be any ordinary halogenating agent capale of converting the hydroxyl group of carboxyl group into a halogen, and can be exemplified by thionyl chloride, oxalyl chloride, phosphorus oxychloride, phosphorus oxybromide, phosphorus pentachloride and phosphorus pentabromide. The proportions of the carboxylic acid (5) and the halogenating agent used are not particularly restricted and can be selected appropriately. When the reaction is conducted using no solvent, the latter is used in a large excess relative to the former; and when the reaction is conducted in a solvent, the latter is used in an amount of generally at least about 1 mole, preferably 2-4 moles per mole of the former. The reaction temperature and the reaction time are not particularly restricted, either, but the reaction is conducted generally at about room temperature to 100° C., preferably at 50°-80° C. for about 30 minutes to 6 hours.

The process which comprises activating a carboxylic acid (5) with a phosphorus compound such as triphenylphosphine, diethyl chlorophosphate, diethyl cyanophosphate or the like, followed by reaction with a compound (4), can be conducted in an appropriate solvent. The solvent can be any solvent which gives no adverse effect on the reaction, and specific examples thereof are halogenated hydrocarbons such as methylene chloride, chloroform, dichloroethane and the like; aromatic hydrocarbons such as benzene, toluene, xylene and the like; ethers such as diethyl ether, tetrahydrofuran, dimethoxyethane and the like; esters such as methyl acetate, ethyl acetate and the like; and aprotic polar solvents such as dimethylformamide, dimethyl sulfoxide, hexamethylphosphoric triamide and the like. Since the compound (4) acts as a basic compound per se, the reaction proceeds favorably by the use of the compound (4) in excess over the stoichiometric amount; however, there may be used, as necessary, other basic compound such as organic base (e.g. triethylamine, trimethylamine, pyridine, dimethylaniline, N-methylmorpholine, 4-dimethylaminopyridine, DBN, DBU or DABCO) or inorganic base (e.g. potassium carbonate, sodium carbonate, potassium hydrogencarbonate or sodium hydrogencarbonate). The reaction is conducted at about 0°-150° C., preferably at about 0°-100° C. and is complete in about 1-30 hours. The proportions of the phosphorus compound and carboxylic acid (5) to the compound (4) are each generally at least about 1 mole, preferably 1-3 moles per mole of the compound (4).

The reaction for converting the compound (6) into a compound (1) can be conducted by reacting the compound (6) in the presence of a sulfurizing agent such as 2,4-bis(4-methoxyphenyl)-1,3-dithia-2,4-diphosphethane-2,4-disulfide (a Lawesson's reagent), phosphorus pentachloride or the like in the absence of any solvent or in the presence of an appropriate solvent. The solvent includes, for example, lower alcohols such as methanol, ethanol, propanol and the like; ethers such as dioxane, tetrahydrofuran, diethyl ether, ethylene glycol monomethyl ether and the like; halogenated hydrocarbons such as dichloromethane, chloroform, carbon tetrachloride and the like; aromatic hydrocarbons such as benzene, toluene, xylene and the like; esters such as ethyl acetate, methyl acetate and the like; ketones such as acetone, methylethyl ketone and the like; polar solvents such as acetonitrile, dimethylformamide, dimethyl sulfoxide, hexamethylphosphoric triamide and the like; and mixtures thereof. The desirable amount of the sulfurizing agent used is generally 0.5-2 moles, preferably 0.5-1.5 moles per mole of the compound (6). The reaction is conducted generally at 50°-300° C., preferably at about 50°-250° C., and is complete in about 1-7 hours.

The compound (2) as a starting material can be produced, for example, by a process represented by the following reaction formula 3 or 4.

[Reaction formula 3]

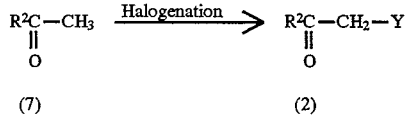

(wherein, $R^2$ and Y are the same as defined above.)

The halogenation reaction for the compound (7) can be conducted in an appropriate solvent in the presence of a halogenating agent. The halogenating agent can be exemplified by molecules of halogens such as bromine, chlorine and the like; iodine chloride; sulfuryl chloride; copper compounds such as cuprous bromide and the like; N-halogenated succinimides such as N-bromosuccinimide, N-chlorosuccinimide and the like. The solvent can be exemplified by halogenated hydrocarbons such as dichloromethane, dichloroethane, chloroform, carbon tetrachloride and the like; fatty acids such as acetic acid, propionic acid and the like; and carbon disulfide. The desirable amount of the halogenating agent used is generally 1-10 moles, preferably 1-5 moles per mole of the compound (7). The reaction is conducted generally at 0° C. to the boiling point of the solvent used, preferably at about 0°-100° C., and is complete generally in about 5 minutes to 20 hours.

[Reaction formula 4]

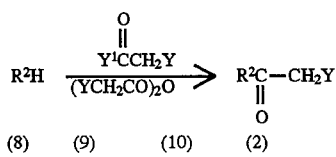

(wherein, $R^2$ and Y are the same as defined above, and $Y^1$ represents a halogen atom.)

The reaction of the compound (8) with the compound (9) or (10) is generally called Friedel-Crafts reaction and can be conducted in an appropriate solvent in the presence of a Lewis acid. The Lewis acid can be any Lewis acid used generally in the Friedel-Crafts reaction, and can be exemplified by aluminum chloride, zinc chloride, iron chloride, tin chloride, boron tribromide, boron trifluoride and concentrated sulfuric acid. The solvent can be exemplified by carbon disulfide; aromatic hydrocarbons such as nitrobenzene, chlorobenzene and the like; and halogenated hydrocarbons such as dichloromethane, dichloroethane, carbon tetrachloride, tetrachloroethane and the like. The desirable amount of the compound (9) or (10) used is at least 1 mole, preferably 1-5 moles per mole of the compound (8). The desirable amount of the Lewis acid used is generally 2-6 moles per mole of the compound (8). The reaction is conducted generally at 0°-120° C., preferably at about 0°-70° C. and is complete in about 0.5-24 hours.

The compound (3) as a starting material can be produced, for example, by a process represented by the following reaction formula 5 or 6.

[Reaction formula 5]

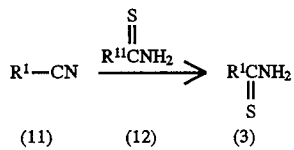

(wherein, $R^1$ is the same as defined above, and $R^{11}$ represents a lower alkyl group.)

The reaction of the compound (11) with the compound (12) can be conducted in an appropriate solvent in the presence of an acid. The solvent can be any solvent used in the above-mentioned reaction of reaction formula 2 for converting a compound (6) into a compound (1). The acid can be exemplified by mineral acids such as hydrochloric acid, hydrobromic acid, sulfuric acid and the like. The desirable amount of the compound (12) used is generally 1–5 moles, preferably 1–3 moles per mole of the compound (11). The reaction is conducted generally at room temperature to 200° C., preferably at about room temperature to 150° C. and is complete in about 1–15 hours.

[Reaction formula 6]

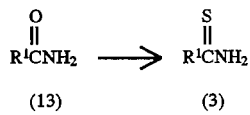

(wherein, $R^1$ is the same as defined above.)

The reaction for converting a compound (13) into a compound (3) can be conducted in an appropriate solvent in the presence of a sulfurizing agent. The solvent can be any solvent used in the above-mentioned reaction of reaction formula 2 for converting a compound (6) into a compound (1). The sulfurizing agent can be exemplified by phosphorus pentasulfide and a Lawesson's reagent. The desirable amount of the sulfurizing agent used is generally 1–10 moles, preferably 1–2 moles per mole of the compound (13). The reaction is conducted generally at room temperature to 150° C., preferably at about room temperature to 100° C. and is complete in about 10 minutes to 5 hours.

A compound (1) wherein $R^3$ is a lower alkoxycarbonyl group or $R^2$ is a 5- to 15-membered monocyclic, bicyclic or tricyclic heterocyclic ring residue having 1–3 nitrogen, oxygen or sulfur atoms having at least one lower alkoxycarbonyl group, can be converted, by hydrolysis, into a corresponding compound wherein $R^3$ is a carboxyl group or $R^2$ is a 5- to 15-membered monocyclic, bicyclic or tricyclic heterocyclic ring residue having 1–3 nitrogen, oxygen or sulfur atoms having at least one carboxyl group.

In the hydrolysis, the conditions employed in ordinary hydrolysis can be used. The hydrolysis is specifically conducted in the presence of, for example, a basic compound (e.g. sodium carbonate, potassium carbonate, sodium hydroxide, potassium hydroxide or barium hydroxide), a mineral acid (e.g. sulfuric acid, hydrochloric acid or nitric acid) or an organic acid (e.g. acetic acid or aromatic sulfonic acid), in a solvent such as water, alcohol (e.g. methanol, ethanol or isopropanol), ketone (e.g. acetone or methyl ethyl ketone), ether (e.g. dioxane or ethylene glycol dimethyl ether), acetic acid or the like, or a mixed solvent thereof. The reaction proceeds generally at room temperature to 200° C., preferably at about room temperature to 180° C. and is complete generally in about 10 minutes to 30 hours.

A compound of general formula (1) wherein $R^2$ is a 5- to 15-membered monocyclic, bicyclic or tricyclic heterocyclic ring having 1–3 nitrogen, oxygen or sulfur atoms having at least one formyl group, can be converted, by reacting the compound (1) with a compound represented by formula (14)

(wherein, $R^{12}$ and $R^{13}$ each represent a lower alkyl group and X represents a halogen atom), into a compound of general formula (1) wherein $R^2$ is a 5- to 15-membered monocyclic, bicyclic or tricyclic heterocyclic ring having 1–3 nitrogen, oxygen or sulfur atoms having at least one oxiranyl group. The reaction is conducted in the presence of a basic compound in an appropriate solvent.

The basic compound (substance) can be exemplified by inorganic bases such as metallic sodium, metallic potassium, sodium hydride, sodium amide, sodium hydroxide, potassium hydroxide, sodium carbonate, potassium carbonate, sodium hydrogencarbonate and the like; metal alcoholates such as sodium methylate, sodium ethylate, potassium tert-butoxide and the like; alkyl- or aryllithiums or lithium amides such as methyllithium, n-butyllithium, phenyllithium, lithium diisopropylamide and the like; and organic bases such as pyridine, piperidine, quinoline, triethylamine, N,N-dimethylaniline and the like. The solvent can be any solvent which gives no adverse effect on the reaction. It includes, for example, ethers such as diethyl ether, dioxane, tetrahydrofuran, monoglyme, diglyme and the like; aromatic hydrocarbons such as benzene, toluene, xylene and the like; aliphatic hydrocarbons such as n-hexane, heptane, cyclohexane and the like; amines such as pyridine, N,N-dimethylaniline and the like; aprotic polar solvents such as N,N-dimethylformamide, dimethyl sulfoxide, hexamethylphosphoric triamide and the like; and alcohols such as methanol, ethanol, isopropanol and the like. The desirable reaction temperature is generally −80° C. to 150° C., preferably about −80° C. to 120° C., and the reaction is complete generally in about 0.5–15 hours.

A compound of general formula (1) wherein $R^2$ is a 5- to 15-membered monocyclic, bicyclic or tricyclic heterocyclic ring having 1–3 nitrogen, oxygen or sulfur atoms having at least one oxiranyl group, can be converted, by hydrolysis or by reacting the compound (1) with a compound represented by formula (15):

(wherein, $R^9$ and $R^{10}$ are the same as defined above), into a compound of general formula (1) wherein $R^2$ is a 5- to 15-membered monocyclic, bicyclic or tricyclic heterocyclic ring having 1–3 nitrogen, oxygen or sulfur atoms having at least one 1,2-dihydroxyethyl group, at least one group of the formula:

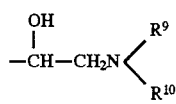

or at least one group of the formula:

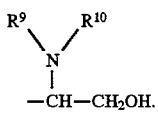

The hydrolysis can be carried out in an appropriate solvent or in the absence of any solvent, in the presence of an acid or a basic compound. The solvent includes, for example, water; lower alcohols such as methanol, ethanol, isopropanol and the like; ketones such as acetone, methyl ethyl ketone and the like; ethers such as dioxane, tetrahydrofuran, ethylene glycol dimethyl ether and the like; fatty acids such as acetic acid, formic acid and the like; dimethyl sulfoxide; and mixed solvents thereof. The acid includes, for example, mineral acids such as hydrochloric acid, sulfuric acid, hydrobromic acid and the like; and organic acids such as formic acid, acetic acid, aromatic sulfonic acids and the like. The basic compound includes, for example, metal carbonates such as sodium carbonate, potassium carbonate and the like; and metal hydroxides such as sodium hydroxide, potassium hydroxide, calcium hydroxide and the like. The reaction proceeds favorably generally at about room temperature to 200° C., preferably at about room temperature to 150° C. and is complete generally in about 0.5–25 hours.

The reaction of the compound of general formula (1) with the compound (15) is conducted generally in an appropriate inert solvent in the presence or absence of a basic compound. The inert solvent includes, for example, aromatic hydrocarbons such as benzene, toluene, xylene and the like; ethers such as tetrahydrofuran, dioxane, diethylene glycol dimethyl ether and the like; lower alcohols such as methanol, ethanol, isopropanol, butanol and the like; acetic acid; ethyl acetate; acetone; acetonitrile; dimethyl sulfoxide; dimethylformamide; and hexamethylphosphoric triamide. The basic compound includes, for example, carbonates such as sodium carbonate, potassium carbonate, sodium hydrogencarbonate, potassium hydrogencarbonate and the like; metal hydroxides such as sodium hydroxide, potassium hydroxide and the like; sodium hydride; potassium and sodium; sodium amide; metal alcoholates such as sodium methylate, sodium ethylate and the like; and organic bases such as pyridine, ethyl-diisopropylamine, dimethylaminopyridine, triethylamine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and the like. The proportions of the compound of general formula (1) and the compound of general formula (15) used are not particularly restricted and can be appropriately selected from a wide range but, desirably, the latter is used in an amount of at least about 1 mole, preferably about 1 mole to a large excess per mole of the former. The reaction is conducted generally at about 0°–200° C., preferably at about 0°–170° C. and is complete generally in about 30 minutes to 30 hours.

A compound of general formula (1) wherein $R^2$ is a 5- to 15-membered monocyclic, bicyclic or tricyclic heterocyclic ring having 1–3 nitrogen, oxygen or sulfur atoms and at least one nitrogen atom of the heterocyclic ring has an oxo group, can be produced by oxidizing a compound of general formula (1) wherein $R^2$ is a 5- to 15-membered monocyclic, bicyclic or tricyclic heterocyclic ring having 1–3 nitrogen, oxygen or sulfur atoms and at least one nitrogen atom of the heterocyclic ring is unsubstituted. The oxidation is conducted in an appropriate solvent in the presence of an oxidizing agent. The solvent can be exemplified by water; organic acids such as formic acid, acetic acid, trifluoroacetic acid and the like; alcohols such as methanol, ethanol and the like; halogenated hydrocarbons such as chloroform, dichloromethane and the like; and mixed solvents thereof. The oxidizing agent includes, for example, peracids such as performic acid, peracetic acid, trifluoroperacetic acid, perbenzoic acid, m-chloroperbenzoic acid, o-carboxyperbenzoic acid and the like; hydrogen peroxide; sodium metaperiodate; bichromic acid; bichromates such as sodium bichromate, potassium bichromate and the like; permanganic acid; permanganates such as potassium permanganate, sodium permanganate and the like; and lead salts such as lead tetraacetate and the like. The oxidizing agent is desirably used in an amount of generally at least 1 mole, preferably 1–2 moles per mole of the starting material. The reaction is conducted generally at 0°–40° C., preferably at about 0° C. to room temperature and is complete in about 1–10 hours.

A compound of general formula (1) wherein $R^2$ is a 5- to 15-membered monocyclic, bicyclic or tricyclic heterocyclic ring having 1–3 nitrogen, oxygen or sulfur atoms and at least one nitrogen atom of the heterocyclic ring has an oxo group, can be converted, by reacting the compound (1) with a compound of formula (16):

(wherein, $R^{14}$, $R^{15}$ and $R^{16}$ each represent a lower alkyl group) or a compound of formula (17):

($R^{17}$ represents a lower alkoxycarbonyl group), into a compound of general formula (1) wherein $R^2$ is a 5- to 15-membered monocyclic, bicyclic or tricyclic heterocyclic ring having 1–3 nitrogen, oxygen or sulfur atoms and the nitrogen atoms have at least one cyano group or at least one group of the formula:

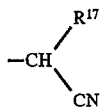

(wherein, $R^{17}$ is the same as defined above).

The reaction of the compound (1) with the compound (17) is conducted in an appropriate solvent in the presence or absence of a basic compound. The basic compound can be exemplified by inorganic bases such as sodium hydroxide, potassium hydroxide, sodium hydrogencarbonate, potassium hydrogencarbonate, sodium carbonate, sodium hydride and the like; metal alcoholates such as sodium methylate, sodium ethylate and the like; organic bases such as triethylamine, pyridine, α-picoline, N,N-dimethylaniline, N-methylmorpholine, piperidine, pyrrolidine and the like. The solvent can be exemplified by ethers such as dioxane, tetrahydrofuran, monoglyme, diglyme and the like; aromatic hydrocarbons such as benzene, toluene, xylene and the like; lower alcohols such as methanol, ethanol, isopropanol and the like; and polar solvents such as dimethyl sulfoxide, dimethylformamide, acetonitrile, acetic anhydride and the like. The reaction is conducted generally at room temperature to 150° C., preferably at 60°–120° C. and is complete in about 1–24 hours. The desirable amount of the compound (17) used is generally 1 mole to a large excess, preferable 1–5 moles per mole of the compound (1). The reaction proceeds favorably when a lower alkanoic acid (e.g. acetic acid), a molecular sieve or the like is added to the reaction system.

The reaction of the compound (1) with the compound (16) can be conducted in an appropriate solvent in the presence of a basic compound. The solvent and basic compound used can each be any of those mentioned with respect to the reaction of the compound (1) with the compound (17). The desirable amount of the compound (16) used is generally 1 mole to a large excess, preferably 1–5 moles per mole of the compound (1). The reaction is conducted generally at room temperature to 150° C., preferably at about room temperature to 100° C. and is complete in about 1–70 hours.

A compound of general formula (1) wherein $R^2$ is a 5- to 15-membered monocyclic, bicyclic or tricyclic heterocyclic ring having 1–3 nitrogen, oxygen or sulfur atoms having at least one cyano group, can be converted, by reacting the compound (1) with sodium azide in an appropriate solvent in the presence of ammonium chloride, into a compound of general formula (1) wherein $R^2$ is a 5- to 15-membered monocyclic, bicyclic or tricyclic heterocyclic ring having 1–3 nitrogen, oxygen or sulfur atoms having at least one 1,2,3,4-tetrazolyl group.

The solvent can be any of those mentioned with respect to the reaction of the compound (1) with the compound (17). The desirable amount of sodium azide used is at least 1 mole, preferably 1–2 moles per mole of the compound (1). The reaction is conducted generally at room temperature to 200° C., preferably at about 50°–150° C. and is complete in about 1–15 hours.

A compound of general formula (1) wherein $R^2$ is a 5- to 15-membered monocyclic, bicyclic or tricyclic heterocyclic ring having 1–3 nitrogen, oxygen or sulfur atoms having at least one cyano group, can be converted, by reacting the compound (1) with a compound of formula (12):

($R^{11}$ is the same as defined above) under the same conditions as in the reaction of the compound (11) with the compound (12) according to the reaction formula 5, into a compound of general formula (1) wherein $R^2$ is a 5- to 15-membered monocyclic, bicyclic or tricyclic heterocyclic ring having 1–3 nitrogen, oxygen or sulfur atoms having at least one aminothiocarbonyl group.

A compound of general formula (1) wherein $R^2$ is a 5- to 15-membered monocyclic, bicyclic or tricyclic heterocyclic ring having 1–3 nitrogen, oxygen or sulfur atoms having at least one aminothiocarbonyl group, can be converted, by alkylation, into a compound of general formula (1) wherein $R^2$ is a 5- to 15-membered monocyclic, bicyclic or tricyclic heterocyclic ring having 1–3 nitrogen, oxygen or sulfur atoms having at least one group of the formula:

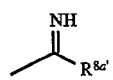

($R^{8a'}$ represents a lower alkylthio group). The alkylation can be conducted in an appropriate solvent in the presence of an alkylating agent in the presence or absence of a basic compound. As to the alkylating agent, there can be mentioned, a compound represented by formula (18):

(wherein, $R^{18}$ represents a lower alkyl group and Ya represents a halogen atom), a dialkyl sulfate (e.g. dimethyl sulfate), etc.

The solvent can be exemplified by lower alcohols such as methanol, ethanol, propanol and the like; ethers such as diethyl ether, tetrahydrofuran, dioxane, ethylene glycol monomethyl ether and the like; halogenated hydrocarbons such as dichloromethane, chloroform, carbon tetrachloride and the like; aromatic hydrocarbons such as benzene, toluene, xylene and the like; esters such as methyl acetate, ethyl acetate and the like; ketones such as acetone, methyl ethyl ketone and the like; polar solvents such as acetonitrile, dimethylformamide, dimethyl sulfoxide, hexamethylphosphoric triamide and the like; and mixed solvents thereof. The basic compound (substance) can be exemplified by inorganic bases such as sodium hydroxide, potassium hydroxide, sodium carbonate, potassium carbonate, sodium hydrogencarbonate, potassium hydrogencarbonate, sodium hydride and the like; alkali metals such as metallic sodium, metallic potassium and the like; alkali metal alcoholates such as sodium ethylate, sodium methylate and the like; and organic bases such as triethylamine, pyridine, piperidine, N,N-dimethylaniline, N-methylmorpholine, diisopropylethylamine, 4-methylaminopyridine, DBN, DBU, DABCO and the like.

When a compound (18) is used as the alkylating agent, there may be used, in the reaction, as necessary a copper powder, a copper halide (e.g. copper iodide) or an alkali metal halide (e.g. sodium iodide or potassium iodide). The compound (18) is used in an amount of generally 1 mole to a large excess, preferably about 1–3 moles per mole of the starting material. The reaction is conducted generally at room temperature to 150° C., preferably at about 50°–120° C. and is complete in about 1–12 hours When a dialkyl sulfate is used as the alkylating agent, the desirable amount of the alkylating agent used is at least 1 mole, preferably about 1–5 moles per mole of the starting material. The reaction is conducted generally at −30° C. to 150° C., preferably at about −20° C. to 100° C. and is complete in about 0.5–20 hours.

A compound of general formula (1) wherein $R^2$ is a 5- to 15-membered monocyclic, bicyclic or tricyclic heterocyclic ring having 1–3 nitrogen, oxygen or sulfur atoms having at least one group of the formula:

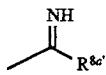

(wherein, $R^{8a'}$ is the same as defined above), can be converted, by reacting the compound (1) with a compound represented by formula (19):

$$R^{19}-NH_2 \qquad (19)$$

(wherein, $R^{19}$ represents a hydrogen atom or a hydroxyl group) in an appropriate solvent, into a compound of general formula (1) wherein $R^2$ is a 5- to 15-membered monocyclic, bicyclic or tricyclic heterocyclic ring having 1–3 nitrogen, oxygen or sulfur atoms having at least one group of the formula:

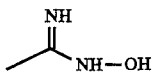

or at least one amidino group. The solvent can be any solvent used in the above alkylation.

The amount of the compound (19) used may be at least 1 mole, preferably 1 mole to a large excess per mole of the starting material. The reaction is conducted generally at 0°–150° C., preferably at about 0°–120° C. and is complete generally in about 1–15 hours. When there is used a compound (19) wherein $R^{19}$ is a hydrogen atom, the reaction is preferably conducted in a sealed tube.

The products thus obtained in each step can be easily separated and purified by ordinary means. The separation means can be exemplified by solvent extraction, dilution, recrystallization, column chromatography and preparative thin-layer chromatography.

Needless to say, the compounds of the present invention include stereoisomers and optical isomers.

The thiazole derivatives represented by general formula (1) of the present invention can be easily converted into acid addition salts by allowing a pharmaceutically acceptable acid to act on said derivatives. The acid addition salts are also included in the present invention. As to the acid, there can be mentioned, for example, inorganic acids such as hydrochloric acid, sulfuric acid, phosphoric acid, hydrobromic acid and the like, as well as organic acids such as acetic acid, oxalic acid, succinic acid, maleic acid, fumaric acid, malic acid, tartaric acid, citric acid, malonic acid, methanesulfonic acid, benzoic acid and the like.

Of the thiazole derivatives represented by general formula (1) of the present invention, those compounds having acidic groups can be easily converted into respective salts by allowing a pharmaceutically acceptable basic compound to act on the compounds. As to the basic compound, there can be mentioned, for example, sodium hydroxide, potassium hydroxide, calcium hydroxide, sodium carbonate and potassium hydrogencarbonate.

The compounds of the present invention are generally used in the form of ordinary pharmaceutical preparations. The pharmaceutical preparations are prepared by using diluents or excipients ordinarily used, such as filler, bulking agent, binder, humectant, disintegrator, surfactant, lubricant and the like. The pharmaceutical preparations can be used in various forms depending upon the purpose of remedy, and typical forms include tablets, pills, powders, solutions, suspensions, emulsions, granules, capsules, suppositories, injections (solutions, suspensions, etc.), ointments, etc. In preparing tablets, various carriers conventionally known in the art can be used. The carriers can be exemplified by excipients such as lactose, white sugar, sodium chloride, glucose, urea, starch, calcium carbonate, kaolin, crystalline cellulose, silicic acid and the like; binders such as water, ethanol, propanol, simple syrup, glucose solution, starch solution, gelatin solution, carboxymethyl cellulose, shellac, methyl cellulose, potassium phosphate, polyvinylpyrrolidone and the like; disintegrators such as dry starch, sodium alginate, powdered agar-agar, powdered laminarin, sodium hydrogencarbonate, calcium carbonate, polyoxyethylene sorbitan-fatty acid esters, sodium lauryl sulfate, stearic acid monoglyceride, starch, lactose and the like; disintegration inhibitors such as white sugar, stearin, cacao butter, hydrogenated oil and the like; absorption promotors such as quaternary ammonium salts, sodium lauryl sulfate and the like; humectants such as glycerine, starch and the like; adsorbents such as starch, lactose, kaolin, bentonite, colloidal silicic acid and the like; and lubricants such as refined talc, stearic acid salts, boric acid powder, polyethylene glycol and the like. The tablets can be prepared, as necessary, in the form of ordinary coated tablets, such as sugar-coated tablets, gelatin-coated tablets, enteric coated tablets or film-coated tablets, or in the form of double-layered tablets or multi-layered tablets. In preparing pills, various carriers conventionally known in the art can be used. The carriers can be exemplified by excipients such as glucose, lactose, starch, cacao butter, hardened vegetable oils, kaolin, talc and the like; binders such as powdered acacia, powdered tragacanth, gelatin, ethanol and the like; and disintegrators such as laminarin, agar-agar and the like. In preparing suppositories, various carriers conventionally known in the art can be used. The carriers can be exemplified by a polyethylene glycol, cacao butter, a higher alcohol, a higher alcohol ester, gelatin and a semi-synthetic glyceride. In preparing injections (solutions, emulsions, suspensions), they are sterilized and are preferably isotonic to the blood. In preparing these solutions, emulsions and suspensions, there can be used all of the diluents conventionally used in the art, such as water, aqueous lactic acid solution, ethyl alcohol, propylene glycol, ethoxylated isostearyl alcohol, polyoxyisostearyl alcohol and polyoxyethylene sorbitan-fatty acid ester. In this case, the injections may contain sodium chloride, glucose or glycerine in an amount sufficient to make the injections isotonic, and may further contain a solubilizing agent, a buffer solution, a soothing agent, etc. all ordinarily used. The pharmaceutical preparations may furthermore contain, as necessary, a coloring agent, a preservative, a perfume, a flavoring agent, a sweetening agent and other drugs. In preparing pastes, creams and gels, there can be used various diluents conventionally used in the art, such as white petrolatum, paraffin, glycerine, cellulose derivative, polyethylene glycol, silicon, bentonite and the like.

The amount of the present compound of the general formula (1) or a salt thereof to be contained in a pharmaceutical preparation is not particularly restricted and can be appropriately selected in a wide range, but preferably is ordinarily 1–70% by weight in the pharmaceutical preparation.

The method for administering the pharmaceutical preparation is not particularly restricted. The pharmaceutical preparation can be administered in various methods depending upon the form of preparation, the age, distinction of sex and other conditions of patient, the degree of disease condition of patient, etc. For example, tablets, pills, a solution, a suspension, an emulsion, granules or capsules are administered orally. An injection is intravenously administered singly or in admixture with an ordinary auxiliary solution of glucose, amino acids or the like, or, as necessary, is singly administered intramuscularly, intradermally, subcutaneously or intraperitoneally. Suppositories are administered intrarectally.

The dose of the pharmaceutical preparation of the present invention is appropriately selected depending upon the administration method, the age, distinction of sex and other conditions of patient, the degree of disease condition of patient, etc., but preferably is ordinarily about 0.2–200 mg per kg of body weight per day in terms of the amount of the active ingredient, i.e. the present compound of general formula (1).

The present invention is hereinafter described more specifically with reference to Reference Examples and Examples.

Reference Example 1

In 120 ml of 10% hydrochloric acid-dimethylformamide were dissolved 29 g of 3,4-diethoxybenzonitrile and 23 g of thioacetamide. The solution was heated at 90° C. for 3 hours and further at 130° C. for 5 hours to conduct a reaction. The reaction mixture was subjected to distillation to remove the solvent. The residue was washed twice with 100 ml of diethyl ether, followed by washing with 100 ml of water. The resulting crystals were collected by filtration and dried to obtain 21.7 g of 3,4-diethoxybenzamide.

NMR spectrum (DMSO-$d_6$) δ ppm: 1.33(6H, t, J=7 Hz), 4.04(2H, q, J=7 Hz), 4.07(2H, q, J=7 Hz), 6.95(1H, d, J=9.1 Hz), 7.65–7.5(2H, m), 9.30(1H, brs), 9.62(1H, brs)

Reference Example 2

0.19 ml of bromine was dropwise added to a solution of 0.88 g of 2-ethoxycarbonyl-3-acetyloxy-6-acetylpyridine dissolved in 8.8 ml of acetic acid. The mixture was stirred at 75° C. for 5 minutes to obtain 0.77 g of 2-ethoxycarbonyl-3-hydroxy-6-(2-bromoacetyl)pyridine hydrobromide.

A brown oily matter $^1$H-NMR (CDCl$_3$) δ ppm: 1.47(3H, t, J=7.1 Hz), 4.48(2H, q, J=7.1 Hz), 4.87(2H, s), 7.45(1H, d, J=8.8 Hz), 8.21(1H, d, J=8.8 Hz), 11.33(1H, s)

The compounds shown in the following Table 1 were obtained in the same manner as in Reference Example 2, using appropriate starting materials.

TABLE 1

$$R^2CCH_2-Y$$
$$\overset{\|}{O}$$

Compound of Reference Example 3

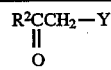

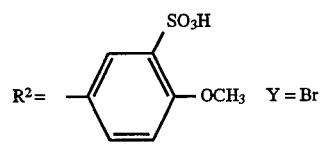

Crystal form: white powder

TABLE 1-continued $$R^2CCH_2-Y$$
$$\overset{\|}{O}$$

Form: free
Compound of Reference Example 4

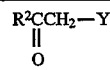

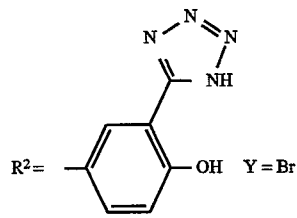

Crystal form: light yellow powder
Form: free
Compound of Reference Example 5

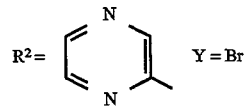

Form: hydrobromide
Compound of Reference Example 6

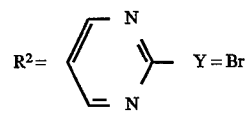

Crystal form: brown solid

The $^1$H-NMR spectral data of the compounds shown in Table 1 are as follows. Compound of Reference Example 3

$^1$H-NMR (DMSO-$d_6$) δ ppm: 3.92(3H, s), 4.84(2H, s), 7.15(1H, d, J=8.7 Hz), 8.06(1H, dd, J=2.4 Hz, 8.7 Hz), 8.36(1H, d, J=2.4 Hz)

Compound of Reference Example 4

$^1$H-NMR (DMSO-$d_6$) δ ppm: 4.91(2H, s), 7.18(1H, d, J=8.7 Hz), 8.07(1H, dd, J=2.3 Hz, 8.7 Hz), 8.63(1H, d, J=2.3 Hz), 12.10(2H, brs)

Compound of Reference Example 5

$^1$H-NMR (DMSO-$d_6$) δ ppm: 5.03(2H, s), 8.83(1H, brs), 8.97(1H, d, J=2.5 Hz), 9.20(1H, d, J=1.4 Hz)

Compound of Reference Example 6

$^1$H-NMR (CDCl$_3$) δ ppm: 4.98(2H, s), 7.77(1H, t, J=4.9 Hz), 9.05(2H, d, J=4.9 Hz)

EXAMPLE 1

0.7 g of 3,4-diethoxythiobenzamide and 20 ml of ethanol were added to 0.77 g of 2-ethoxycarbonyl-3-hydroxy-6-(2-bromoacetyl)pyridine. The mixture was refluxed for 3 hours. Ethanol was removed by distillation. To the residue was added ethyl acetate-dichloromethane to give rise to crystallization to obtain 0.62 g of 2-(3,4-diethoxyphenyl)-4-(5-hydroxy-6-ethoxycarbonyl-2-pyridyl)thiazole.

A gray powder $^1$H-NMR (DMSO-$d_6$) δ ppm: 1.35–1.44(9H, m), 4.07–4.22(4H, m), 4.37(2H, q, J=7.1 Hz), 5.67(1H, brs), 7.08(1H, d, J=8.4 Hz), 7.52–7.57(2H, m), 7.55(1H, d, J=8.7 Hz), 8.04(1H, s), 8.27(1H, d, J=8.7 Hz)

EXAMPLE 2

A solution of 0.32 g of sodium hydroxide dissolved in 20 ml of ethanol and 20 ml of water was added to 0.54 g of 2-(3,4-diethoxyphenyl)-4-(5-hydroxy-6-ethoxycarbonyl-2-pyridyl)thiazole. The mixture was refluxed for 2.5 hours. To the reaction mixture was added 100 ml of water. The mixture was made acidic with concentrated hydrochloric acid and subjected to extraction four times with 70 ml of ethyl acetate. The solvent in the extract was removed and the resulting residue was recrystallized from ethyl acetate-diethyl ether to obtain 0.24 g of 2-(3,4-diethoxyphenyl)-4-(5-hydroxy-6-carboxy-2-pyridyl)thiazole. m.p.: 161.4°–162° C.

A light brown powder

The following compounds were obtained in the same manner as in Example 1, using appropriate starting materials.

TABLE 2

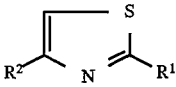

Compound of Example 3

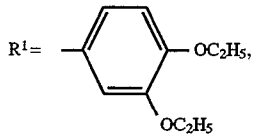

Crystal form: white powder
m.p.: 175.5–179.5° C.

Recrystallization solvent: acetone
Form: hydrochloride

Compound of Example 4

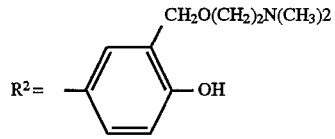

Crystal form: brown amorphous
Form: hydrochloride

Compound of Example 5

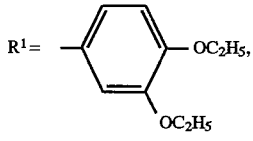

Crystal form: white needle
m.p.: 161–162° C.

Recrystallization solvent: ethyl acetate
Form: free

Compound of Example 6

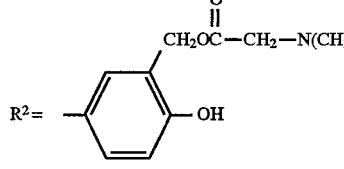

Crystal form: white plate
m.p.: 175–177.5° C.

Recrystallization solvent: ethyl acetate
Form: free

TABLE 3

Compound of Example 7

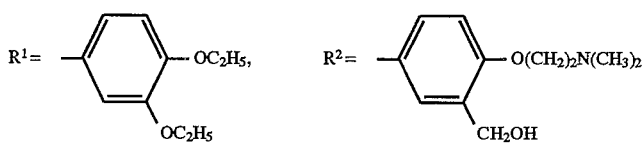

TABLE 3-continued

Crystal form: light yellow powder
m.p.: 148–151° C.
Compound of Example 8

Recrystallization solvent: acetone
Form: dihydrochloride

R¹= 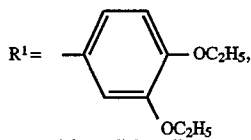 ,

R²= 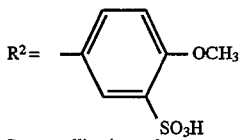

Crystal form: light yellow prism
m.p.: 265.2–267.2° C
Compound of Example 9

Recrystallization solvent: water
Form: free

R¹= 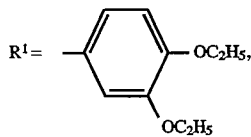 ,

R²= 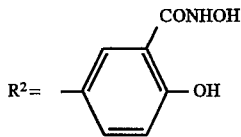

Crystal form: white powder
m.p.: 139.5–140° C.
Compound of Example 10

Recrystallization solvent: n-hexane-ethyl acetate
Form: free

R¹= 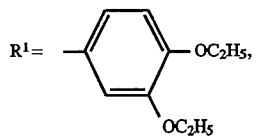 ,

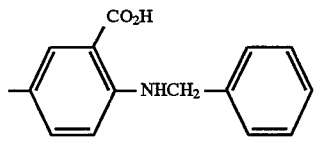

Crystal form: yellow amorphous

TABLE 4

Compound of Example 11

R¹= 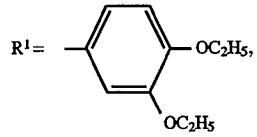 ,

R²= 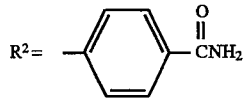

Crystal form: white needle m.p.: 212–213° C.
Compound of Example 12

Recrystallization solvent:
ethyl acetate
Form: free

R¹= 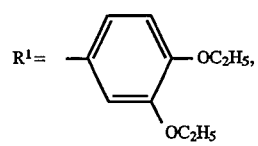 ,

R²= 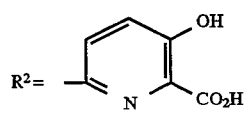

Crystal form: light brown powder
m.p.: 161.4–162° C.

Recrystallization solvent: ethyl acetate-diethyl ether
Form: free

TABLE 4-continued

Compound of Example 13

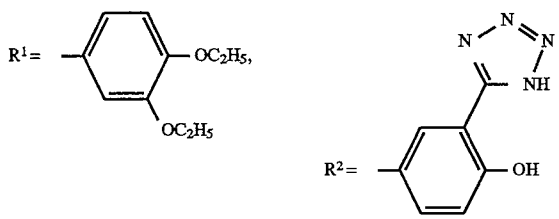

Crystal form: orange powder
m.p.: 223.2–226.4° C. (decomp.)

Recrystallization solvent: ethanol-ethyl acetate
Form: free

Compound of Example 14

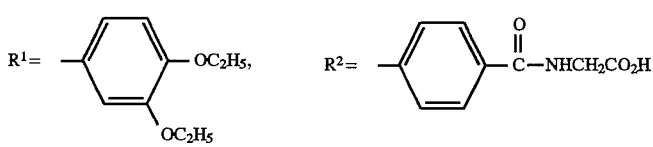

Crystal form: white needle
m.p.: 189–190° C.

Recrystallization solvent: methanol
Form: free

TABLE 5

Compound of Example 15

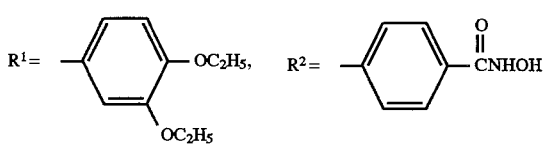

Crystal form: white needle
m.p.: 200–201° C.

Recrystallization solvent: methanol
Form: free

Compound of Example 16

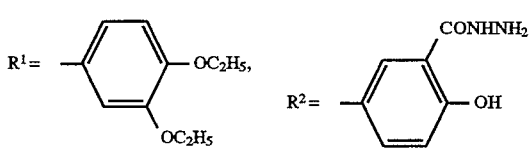

Crystal form: white powder
m.p.: 158–161.5° C.

Recrystallization solvent: ethanol-water
Form: free

Compound of Example 17

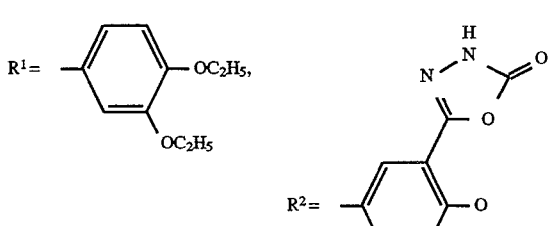

Crystal form: white powder
m.p.: 204–205° C.

Recrystallization solvent: ethyl acetate
Form: free

TABLE 5-continued

Compound of Example 18

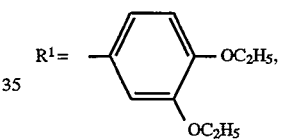 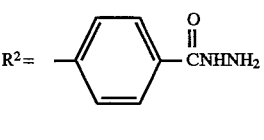

Crystal form: white needle
m.p.: 185–186° C.

Recrystallization solvent: methanol
Form: free

TABLE 6

Compound of Example 19

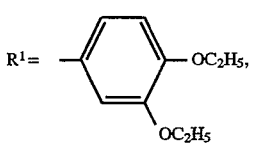 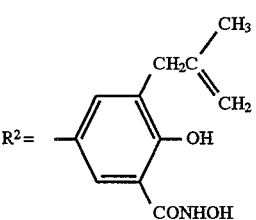

Crystal form: light red powder
m.p.: 154.5–156.5° C.

Recrystallization solvent: ethanol-diethyl ether
Form: free

Compound of Example 20

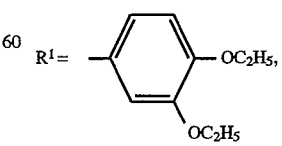 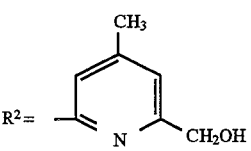

Crystal form: light yellow needle

Recrystallization solvent: ethyl acetate-n-hexane

TABLE 6-continued m.p.: 116–117° C.
Compound of Example 21

R¹= 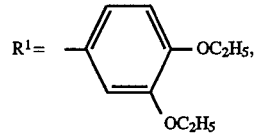

R²= 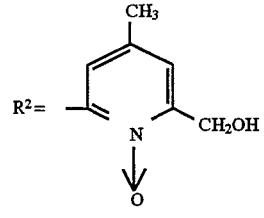

Crystal form: white plate
m.p.: 178–179° C.
Compound of Example 22

Recrystallization solvent: methanol
Form: free

R¹= 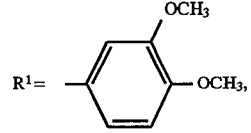

R²= 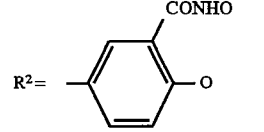

Crystal form: light brown grain
m.p.: 185–186° C.

Recrystallization solvent: ethanol
Form: 2Na⁺

TABLE 7

Compound of Example 23

R¹= 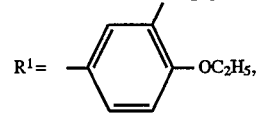

R²= 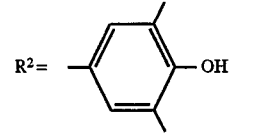

Crystal form: white needle
m.p.: 148.5–150° C.
Compound of Example 24

Recrystallization solvent: n-hexane-ethyl acetate
Form: free

R¹= 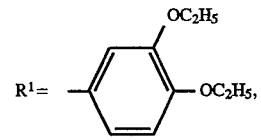

R²= 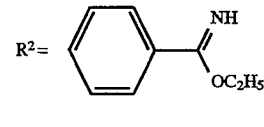

Crystal form: light yellow needle
m.p.: 110–111° C.
Compound of Example 25

Recrystallization solvent: n-hexane-ethyl acetate
Form: free

R¹= 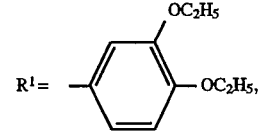

R²= 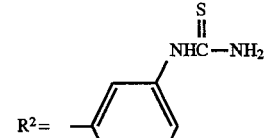

Crystal form: white powder
m.p.: 193–195° C.

Recrystallization solvent: ethyl acetate
Form: free

TABLE 7-continued

Compound of Example 26

R¹= 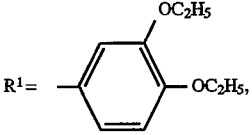

R²= 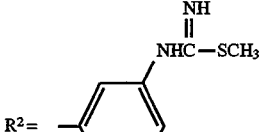

Crystal form: light yellow powder
m.p.: 204–208° C.

Recrystallization solvent: methanol
Form: hydroiodide

TABLE 8

Compound of Example 27

R¹= 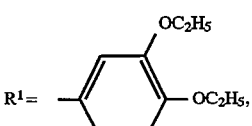

R²= 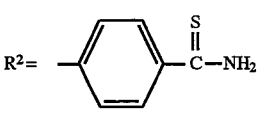

Crystal form: light yellow powder
m.p.: 200–203° C.
Compound of Example 28

Recrystallization solvent: n-hexane-ethyl acetate
Form: free

R¹= 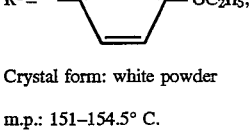

R²= 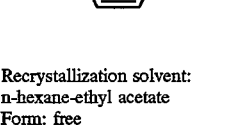

Crystal form: white powder
m.p.: 151–154.5° C.
Compound of Example 29

Recrystallization solvent: n-hexane-ethyl acetate
Form: free

R¹= 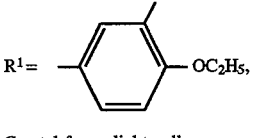

R²= 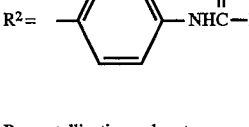

Crystal form: light yellow powder
m.p.: 195–197° C.
Compound of Example 30

Recrystallization solvent: benzene
Form: monomethylsulfate

R¹= 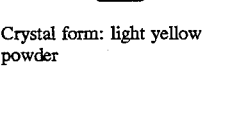

R²= 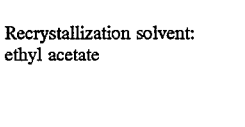

Crystal form: light yellow powder
m.p.: 182–185° C.
Compound of Example 31

Recrystallization solvent: ethanol
Form: free

R¹= 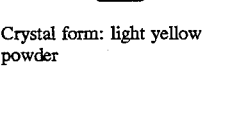

R²= 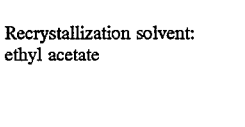

Crystal form: light yellow powder

Recrystallization solvent: ethyl acetate

TABLE 8-continued m.p.: 189° C. (decomp.)    Form: hydrochloride

TABLE 9

Compound of Example 32

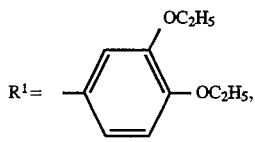 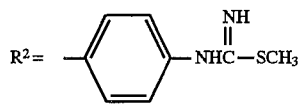

Crystal form: light green
needle
m.p.: 157–159° C.

Recrystallization solvent:
benzene
Form: monomethylsulfate

Compound of Example 33

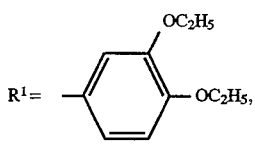 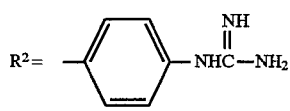

Crystal form: white powder m.p.: 257–260° C.

Recrystallization solvent:
methanol
Form: monomethylsulfate

Compound of Example 34

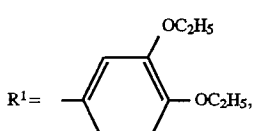 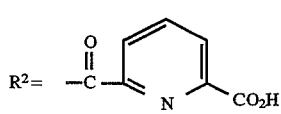

Crystal form: light brown
powder
m.p.: 177–178° C.

Recrystallization solvent:
ethyl acetate
Form: free

Compound of Example 35

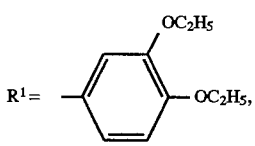 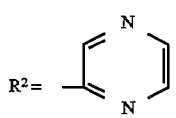

Crystal form: yellow needle m.p.: 119–120° C.

Recrystallization solvent:
ethanol
Form: free

Compound of Example 36

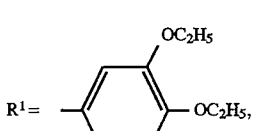 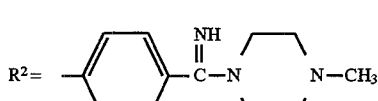

Crystal form: white powder m.p.: 207–210° C.

Recrystallization solvent:
acetone
Form: trihydrochloride

TABLE 10

Compound of Example 37

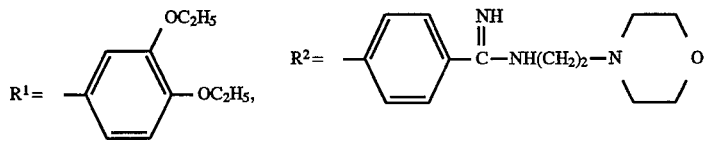

Crystal form: light yellow amorphous
Form: dihydrochloride

Compound of Example 38

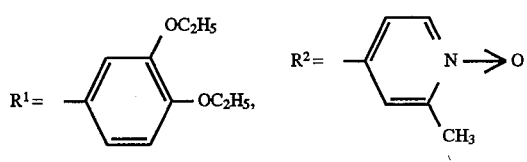

Crystal form: brown solid
Form: free

Compound of Example 39

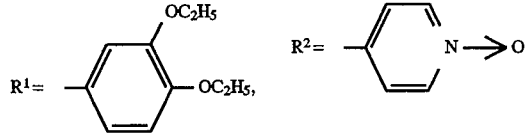

Crystal form: yellow solid
Form: free

Compound of Example 40

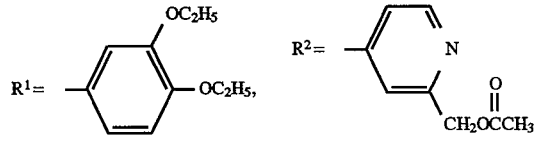

Crystal form: brown oil
Form: free

[TABLE 11]

Compound of Example 41

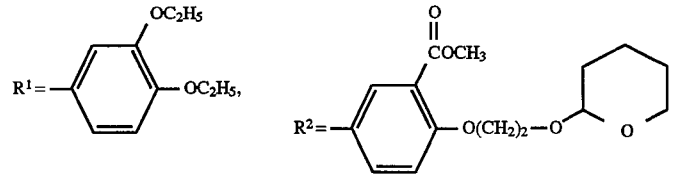

Crystal form: colorless oil
Form: free

Compound of Example 42

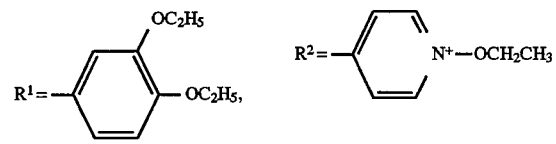

Crystal form: light yellow powder
Form: I$^-$

[TABLE 11]-continued

Compound of Example 43

R¹= 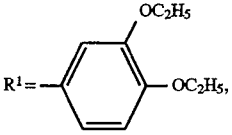 (OC₂H₅, OC₂H₅),  R²= 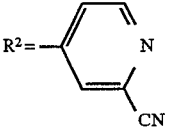 (pyridine with CN)

Crystal form: white powder
Form: free
Recrystallization solvent: ethanol-water

Compound of Example 44

R¹= 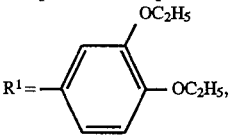 (OC₂H₅, OC₂H₅),  R²= 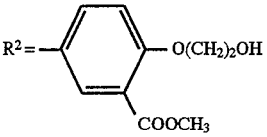 —O(CH₂)₂OH, COOCH₃

Crystal form: white needle
Form: free
Recrystallization solvent: ethyl acetate-n-hexane

[TABLE 12]

Compound of Example 45

R¹= 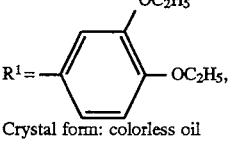 (OC₂H₅, OC₂H₅),  R²= 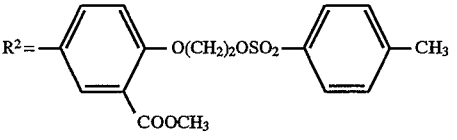 —O(CH₂)₂OSO₂—⟨ ⟩—CH₃, COOCH₃

Crystal form: colorless oil
Form: free

Compound of Example 46

R¹= 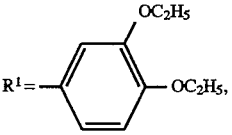 (OC₂H₅, OC₂H₅),  R²= 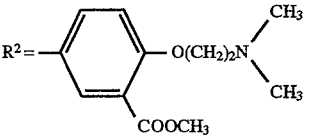 —O(CH₂)₂N(CH₃)₂, COOCH₃

Crystal form: yellow oil
Form: free

Compound of Example 47

R¹= 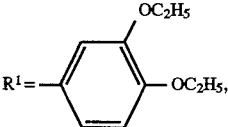 (OC₂H₅, OC₂H₅),  R²= 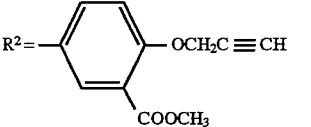 —OCH₂C≡CH, COOCH₃

Crystal form: white needle
m.p.: 102–103° C.
Recrystallization solvent: ethanol
Form: free Compound of Example 48

R¹= 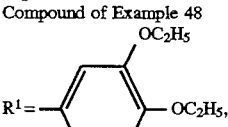 (OC₂H₅, OC₂H₅),  R²= 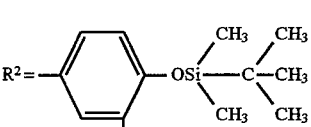 —OSi—C(CH₃)₃(CH₃)₂, CH₂OCOCH₂N(CH₃)₂

Crystal form: colorless oil
Form: free

[TABLE 13]

Compound of Example 49

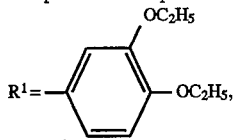
R¹ =

Form: free

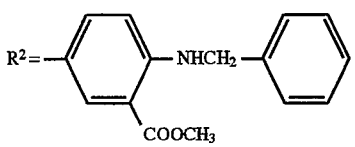
R² =

Compound of Example 50

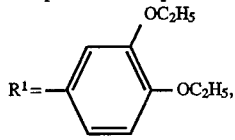
R¹ =

Crystal form: white grain m.p.: 77–80.5° C.

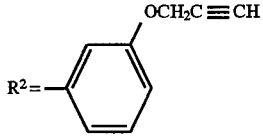
R² =

Recrystallization solvent: ethanol
Form: free

Compound of Example 51

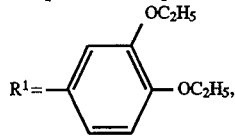
R¹ =

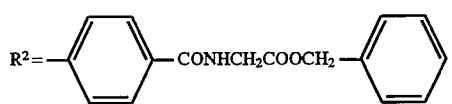
R² =

Crystal form: white needle m.p.: 145–146° C.

Recrystallization solvent: ethanol
Form: free

Compound of Example 52

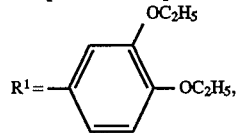
R¹ =

Crystal form: light brown oil
Form: free

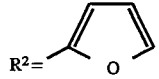
R² =

Compound of Example 53

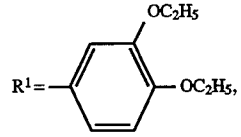
R¹ =

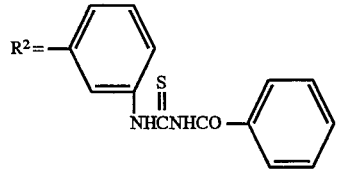
R² =

Crystal form: light yellow powder
m.p.: 185–186° C.

Recrystallization solvent: ethanol
Form: free

[TABLE 14]

Compound of Example 54

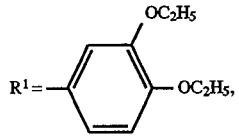
R¹ =

Crystal form: yellow powder m.p.: 174–177° C.

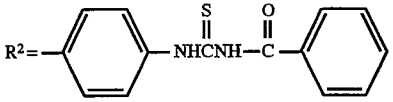
R² =

Recrystallization solvent: water
Form: free

[TABLE 14]-continued

Compound of Example 55

R¹ = (3,4-diethoxyphenyl, OC₂H₅, OC₂H₅)

Crystal form: light yellow powder
m.p.: 196–198° C.

R² = (4-substituted phenyl)—C(=NH)—SCH₃

Recrystallization solvent: dichloromethane-diethyl ether
Form: trifluoromethanesulfonate Compound of Example 56

R¹ = (3,4-diethoxyphenyl, OC₂H₅, OC₂H₅)

Crystal form: brown needle
m.p.: 115–116° C.

R² = —C(=O)—(pyridine-2-yl with COOC₂H₅)

Recrystallization solvent: ethanol
Form: free

Compound of Example 57

R¹ = (3,4-diethoxyphenyl, OC₂H₅, OC₂H₅)

Crystal form: brown oil
Form: free

R² = (furan / isoxazoline with COOCH₂CH₃)

Compound of Example 58

R¹ = (3,4-diethoxyphenyl, OC₂H₅, OC₂H₅)

Crystal form: colorless needle
m.p.: 114–115° C.

R² = (2-chloropyridin-6-yl)

Recrystallization solvent: ethyl acetate-n-hexane
Form: free

[TABLE 15]

Compound of Example 59

R¹ = (3,4-diethoxyphenyl, OC₂H₅, OC₂H₅)

Crystal form: light brown needle
m.p.: 115–116° C.

R² = (4-chloropyridin-2-yl)

Recrystallization solvent: ethyl acetate-n-hexane
Form: free

Compound of Example 60

R¹ = (3,4-diethoxyphenyl, OC₂H₅, OC₂H₅)

Crystal form: brown oil

R² = (pyridinyl with CH₂OH)

Compound of Example 61

R¹ = (3,4-diethoxyphenyl, OC₂H₅, OC₂H₅)

Crystal form: brown solid

R² = (3-pyridinyl with CO₂CH₃)

Compound of Example 62

R¹ = (3,4-diethoxyphenyl, OC₂H₅, OC₂H₅)

Crystal form: brown solid

R² = (imidazole with CO₂C₂H₅, NH)

[TABLE 16]

| Compound | R¹ | R² | Properties |
|---|---|---|---|
| Compound of Example 63 | 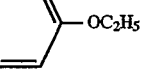 | 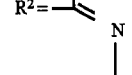 | Crystal form: light yellow needle<br>m.p.: 121–123.5° C.<br>Recrystallization solvent: ethyl acetate<br>Form: free |
| Compound of Example 64 | 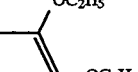 | 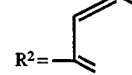 | Crystal form: white needle<br>m.p.: 121.5–122° C.<br>Recrystallization solvent: ethyl acetate-n-hexane<br>Form: free |
| Compound of Example 65 | 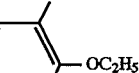 | 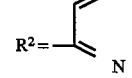 | Crystal form: yellow needle<br>m.p.: 185.5–187.5° C.<br>Recrystallization solvent: ethanol-diethyl ether<br>Form: dihydrochloride |
| Compound of Example 66 | 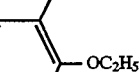 | 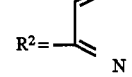 | Crystal form: light yellow powder<br>m.p.: 178–179° C.<br>Recrystallization solvent: ethanol-diethyl ether<br>Form: dihydrochloride |

[TABLE 17]

| Compound | R¹ | R² | Properties |
|---|---|---|---|
| Compound of Example 67 | 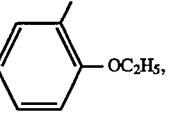 | 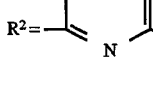 | Crystal form: yellow needle<br>m.p.: 161–163° C.<br>Recrystallization solvent: ethanol-diethyl ether<br>Form: dihydrochloride |
| Compound of Example 68 | 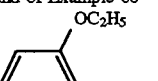 | 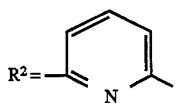 | Crystal form: light yellow needle<br>m.p.: 214–215.5° C.<br>Recrystallization solvent: ethanol-diethyl ether<br>Form: hydrochloride |
| Compound of Example 69 | 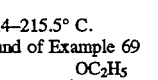 | 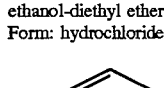 | Crystal form: colorless needle<br>m.p.: 108–109° C.<br>Recrystallization solvent: diisopropyl ether<br>Form: free |

Compound of Example 4

¹H-NMR (DMSO-d₆) δ ppm: 1.16–1.76(6H, m), 2.49(1H, s), 3.23(6H, brs), 3.87–4.22(4H, m), 4.29(2H, brs), 4.75(2H, brs), 7.06(1H, d, J=9.0 Hz), 7.18(1H, d, J=8.2 Hz), 7.52(2H, brs), 7.88(1H, s), 7.97–8.06(2H, m), 10.95(1H, brs)

Compound of Example 10

¹H-NMR (CDCl₃) δ ppm: 1.44(3H, t, J=7.0 Hz), 1.46(3H, t, J=7.0 Hz), 4.09(2H, q, J=7.0 Hz), 4.12(2H, q, J=7.0 Hz), 4.61(2H, d, J=5.6 Hz), 6.87(1H, d, J=8.2 Hz), 7.03(1H, brs), 7.05(1H, d, J=8.6 Hz), 7.26–7.32(6H, m), 7.44–7.51(2H, m), 7.87(1H, dd, J=2.2 Hz, 8.6 Hz), 8.18(1H, s), 12.55(1H, s)

Compound of Example 37

¹H-NMR (DMSO-d₆) δ ppm: 1.39(3H, t, J=7.0 Hz), 1.41(3H, t, J=7.0 Hz), 3.05–4.08(12H, m), 4.13(2H, q, J=7.0 Hz), 4.18(2H, q, J=7.0 Hz), 7.11(1H, d, J=8.2 Hz), 7.55–7.60 (2H, m), 8.04(2H, d, J=8.5 Hz), 8.29(2H, d, J=8.5 Hz), 8.42(1H, s), 9.65(1H, brs), 9.91(1H, brs), 10.21(1H, brs), 11.56(1H, brs )

Compound of Example 38

¹H-NMR (CDCl₃) δ ppm: 1.45(3H, t, J=7.0 Hz), 1.47(3H, t, J=7.0 Hz), 2.63(3H, s), 4.10–4.26(4H, m), 6.88(1H, d, J=8.4 Hz), 7.35–7.50(2H, m), 7.89–8.10(3H, m), 8.40(1H, d, J=6.7 Hz)

Compound of Example 39

¹H-NMR (DMSO-d₆) δ ppm: 1.35(3H, t, J=6.9 Hz), 1.37(3H, t, J=6.9 Hz), 4.07–4.21(4H, m), 7.07(1H, d, J=8.3 Hz), 7.52(1H, dd, J=2.1 Hz, 8.3 Hz), 7.59(1H, d, J=2.1 Hz), 8.03(2H, d, J=7.2 Hz), 8.29(2H, d, J=7.2 Hz), 8.33(1H, s)

Compound of Example 40

¹H-NMR (CDCl₃) δ ppm: 1.46(3H, t, J=7.0 Hz), 1.47(3H, t, J=7.0 Hz), 2.19(3H, s), 4.10–4.25(4H, m), 5.34(2H, s), 6.89(1H, d, J=8.4 Hz), 7.37(1H, dd, J=2.2 Hz, 8.4 Hz), 7.49(1H, d, J=2.2 Hz), 7.95–8.10(3H, m), 8.73(1H, dd, J=0.7 Hz, 5.2 Hz)

Compound of Example 41

¹H-NMR (CDCl₃) δ ppm: 1.41–1.86(6H, m), 1.49(3H, t, J=6.5 Hz), 1.51(3H, t, J=6.5 Hz), 3.52–3.57(1H, m), 3.85–3.94(2H, m), 3.92(3H, s), 4.06–4.30(7H, m), 4.77(1H, t, J=3.2 Hz), 6.91(1H, d, J=8.4 Hz), 7.08(1H, d, J=8.7 Hz), 7.35(1H, s), 7.52(1H, dd, J=1.8 Hz, 8.4 Hz), 7.61(1H, d, J=1.8 Hz), 8.10(1H, dd, J=2.1 Hz, 8.7 Hz), 8.35(1H, d, J=2.1 Hz)

Compound of Example 42

¹H-NMR (DMSO-d₆) δ ppm: 1.36–1.48(9H, m), 4.13–4.20(4H, m), 4.69(2H, q, J=6.9 HZ), 7.12(1H, d, J=8.8 Hz), 7.61–7.65(2H, m), 8.75(2H, d, J=7.1 Hz), 9.05(1H, s), 9.47(2H, d, J=7.1 Hz)

Compound of Example 43

¹H-NMR (DMSO-d₆) δ ppm: 1.39(3H, t, J=6.9 Hz), 1.41(3H, t, J=6.9 Hz), 4.12–4.27(4H, m), 7.13(1H, d, J=8.2 Hz), 7.61–7.67(2H, m), 8.38(1H, dd, J=1.3 Hz, 5.2 Hz), 8.64(2H, s), 8.84(1H, d, J=5.2 Hz)

Compound of Example 44

¹H-NMR (CDCl₃) δ ppm: 1.49(3H, t, J=7.0 Hz), 1.51(3H, t, J=7.0 Hz), 3.72(1H, brs), 3.94(5H, s), 4.16(2H, q, J=7.0 Hz), 4.22(2H, q, J=7.0 Hz), 4.28(2H, t, J=4.1 Hz), 6.92(1H, d, J=8.4 Hz), 7.09(1H, d, J=8.7 Hz), 7.37(1H, s), 7.53(1H, dd, J=2.1 Hz, 8.3 Hz), 7.61(1H, d, J=2.1 Hz), 8.13(1H, dd, J=2.4 Hz, 8.7 Hz), 8.40(1H, d, J=2.3 Hz)

Compound of Example 45

¹H-NMR (CDCl₃) δ ppm: 1.49(3H, t, J=7.0 Hz), 1.51(3H, t, J=7.0 Hz), 2.42(3H, s), 3.90(3H, s), 4.15(2H, q, J=7.0 Hz), 4.20(2H, q, J=7.0 Hz), 4.26–4.31(2H, m), 4.40–4.44(2H, m), 6.92(1H, d, J=8.5 Hz), 6.96(1H, d, J=8.8 Hz), 7.33(2H, d, J=8.0 Hz), 7.36(1H, s), 7.52(1H, dd, J=2.1 Hz, 8.5 Hz), 7.61(1H, d, J=2.1 Hz), 7.82(2H, d, J=8.0 Hz), 8.07(1H, dd, J=2.4 Hz, 8.8 Hz), 8.35(1H, d, J=2.4 Hz)

Compound of Example 46

¹H-NMR (CDCl₃) δ ppm: 1.49(3H, t, J=7.0 Hz), 1.51(3H, t, J=7.0 Hz), 2.44(6H, s), 2.89(2H, t, J=5.7 Hz), 3.92(3H, s), 4.02–4.27(6H, m), 6.92(1H, d, J=8.4 Hz), 7.05(1H, d, J=8.7 Hz), 7.35(1H, s), 7.52(1H, dd, J=2.0 Hz, 8.3 Hz), 7.61(1H, d, J=2.0 Hz), 8.11(1H, dd, J=2.3 Hz, 8.7 Hz), 8.37(1H, d, J=2.3 Hz)

Compound of Example 48

¹H-NMR (CDCl₃) δ ppm: 0.27(6H, s), 1.02(9H, s), 1.49 (3H, t, J=7.0 Hz), 1.51(3H, t, J=7.0 Hz), 2.38(6H, s), 3.23(2H, s), 4.15(2H, q, J=7.0 Hz), 4.22(2H, q, J=7.0 Hz), 5.23(2H, s), 6.90(1H, d, J=8.4 Hz), 6.92(1H, d, J=8.4 Hz), 7.28(1H, s), 7.51(1H, dd, J=2.1 Hz, 8.4 Hz), 7.62(1H, d, J=2.1 Hz), 7.85(1H, dd, J=2.3 Hz, 8.4 Hz), 7.93(1H, d, J=2.3 Hz)

Compound of Example 49

¹H-NMR (CDCl₃) δ ppm: 1.47(3H, t, J=7.0 Hz), 1.49(3H, t, J=7.0 Hz), 3.90(3H, s), 4.12(2H, q, J=7.0 Hz), 4.20(2H, q, J=7.0 Hz), 4.50(2H, d, J=5.6 Hz), 6.71(1H, d, J=8.8 Hz), 6.90(1H, d, J=8.4 Hz), 7.25–7.39(6H, m), 7.51(1H, dd, J=2.1 Hz, 8.4 Hz), 7.59(1H, d, J=2.1 Hz), 7.93(1H, dd, J=2.2 Hz, 8.8 Hz), 8.28(1H, t, J=5.6 Hz), 8.52(1H, d, J=2.2 Hz)

Compound of Example 52

¹H-NMR (CDCl₃) δ ppm: 1.49(3H, t, J=7.0 Hz), 1.51(3H, t, J=7.0 Hz), 4.18(2H, q, J=7.0 Hz), 4.42(2H, q, J=7.0 Hz), 6.57(1H, dd, J=1.8 Hz, 3.6 Hz), 6.95(1H, d, J=8.5 Hz), 7.48(1H, s), 7.51(1H, d, J=1.3 Hz), 7.79(1H, dd, J=2.3 Hz, 8.5 Hz), 8.26(1H, d, J=2.3 Hz), 8.46(1H, d, J=3.6 Hz)

Compound of Example 57

¹H-NMR (CDCl₃) δ ppm: 1.48(3H, t, J=7.0 Hz), 1.50(6H, t, J=7.0 Hz), 2.85(1H, dd, J=7.3 Hz, 19.2 Hz), 2.95(1H, dd, J=1.9 Hz, 19.2 Hz), 3.50–3.63(1H, m), 4.05–4.48(6H, m), 4.85–5.02(1H, m), 6.87(1H, d, J=8.2 Hz), 7.35–7.55(3H, m)

Compound of Example 60

¹H-NMR (CDCl₃) δ ppm: 1.45(3H, t, J=7.0 Hz), 1.46(3H, t, J=7.0 Hz), 4.10–4.24(5H, m), 4.85(2H, s), 6.88(1H, d, J=8.4 Hz), 7.36(1H, dd, J=2.2 Hz, 8.4 Hz), 7.47(1H, d, J=2.2 Hz), 7.88–7.91(2H, m), 8.62(1H, d, J=8.3 Hz)

Compound of Example 61

¹H-NMR (CDCl₃) δ ppm: 1.44(3H, t, J=7.0 Hz), 1.47(3H, t, J=7.0 Hz), 3.81(3H, s), 4.10–4.24(4H, m), 6.93(1H, d, J=8.4 Hz), 7.46–7.55(3H, m), 8.00(1H, dd, J=1.6 Hz, 7.8 Hz), 8.21(1H, s)

Compound of Example 62

¹H-NMR (CDCl₃ ) δ ppm: 1.34(3H, t, J=7.1 Hz), 3.88 (3H, s), 3.93(3H, s), 4.32(2H, q, J=7.1 Hz), 7.47–7.53(2H, m), 7.78(1H, s), 7.99(1H, s), 12.03(1H, brs)

EXAMPLE 70

2-(3,4-Diethoxyphenyl)-4-[4-(1-morpholino-1-iminomethyl)phenyl]thiazole was obtained in the same manner as in Example 1, by using 4'-(1-morpholino-1-iminomethyl)-2-bromoacetophenone and 3,4-diethoxythiobenzamide.

EXAMPLE 71

2-(3,4-Diethoxyphenyl)-4-(3-amidinoaminophenyl) thiazole was obtained in the same manner as in Example 1, by using 3'-amidinoamino-2-bromoacetophenone and 3,4-diethoxythiobenzamide.

EXAMPLE 72

6-[2-(3,4-Diethoxyphenyl)-4-thiazolyl]pyridine-2-carbohydroxamic acid was obtained in the same manner as in Example 1, by using 6-(hydroxyaminocarbonyl)-2-(α-bromoacetyl)pyridine and 3,4-diethoxythiobenzamide.

A white powder (recrystallized from ethyl acetate)
m.p.: 208°–210° C.

EXAMPLE 73

2-(3,4-Diethoxyphenyl)-4-{6-[1-(2-pyridyl)-1-hydroxymethyl]-2-pyridyl}thiazole was obtained in the same manner as in Example 1, by using 6-[1-(2-pyridyl)-1-hydroxymethyl]-2-(α-bromoacetyl)pyridine and 3,4-diethoxythiobenzamide.

EXAMPLE 74

2-(3,4-Diethoxyphenyl)-4-{6-[1-(2-furyl)-1-hydroxymethyl]-2-pyridyl}thiazole was obtained in the same manner as in Example 1, by using 6-[1-(2-furyl)-1-hydroxymethyl]-2-(α-bromoacetyl)pyridine and 3,4-diethoxythiobenzamide.

EXAMPLE 75

2-(3,4-Diethoxyphenyl)-4-(6-carboxymethyl-2-pyridyl)thiazole was obtained in the same manner as in Example 1, by using 6-carboxymethyl-2-(α-bromoacetyl)pyridine and 3,4-diethoxythiobenzamide.

EXAMPLE 76

2-(3,4-Diethoxyphenyl)-4-[6-(2-carboxyethyl)-2-pyridyl]thiazole was obtained in the same manner as in Example 1, by using 6-(2-carboxyethyl)-2-(α-bromoacetyl)pyridine and 3,4-diethoxythiobenzamide.

EXAMPLE 77

2-(3,4-Diethoxyphenyl)-4-(6-dimethylaminomethyl-2-pyridyl)thiazole dihydrochloride was obtained in the same manner as in Example 1, by using 6-dimethylaminomethyl-2-(α-bromoacetyl)pyridine and 3,4-diethoxythiobenzamide A yellow powder (recrystallized from diethyl etherethanol)

m.p.: 195° C. (decomp.)

EXAMPLE 78

2-(3,4-Diethoxyphenyl)-4-(6-cyanomethyl-2-pyridyl)thiazole was obtained in the same manner as in Example 1, by using 6-cyanomethyl-2-(α-bromoacetyl)pyridine and 3,4-diethoxythiobenzamide.

EXAMPLE 79

A reaction was conducted in the same manner as in Example 1, by using 5-ethoxycarbonyl-2-(α-bromoacetyl)pyrazine and 3,4-diethoxythiobenzamide. Then, hydrolysis was conducted in the same manner as in Example 2 to obtain 2-(3,4-diethoxyphenyl)-4-(5-carboxy-2-pyrazinyl)thiazole.

A white powder (recrystallized from ethyl acetate)

$^1$H-NMR (DMSO-$d_6$) δ ppm: 1.39(3H, t, J=7.0 Hz), 1.41(3H, t, J=7.0 Hz), 4.13(2H, q, J=7.0 Hz), 4.19(2H, q, J=7.0 Hz), 7.11(1H, d, J=8.5 Hz), 7.52–7.72(2H, m), 8.49 (1H, s), 9.18(1H, s), 9.60(1H, s), 13.83(1H, brs)

EXAMPLE 80

A reaction was conducted in the same manner as in Example 1, by using 4-ethoxycarbonyl-2-(α-bromoacetyl)pyrimidine and 3,4-diethoxythiobenzamide. Then, hydrolysis was conducted in the same manner as in Example 2 to obtain 2-(3,4-diethoxyphenyl)-4-(4-carboxy-2-pyrimidyl)thiazole.

EXAMPLE 81

A reaction was conducted in the same manner as in Example 1, by using 5-ethoxycarbonyl-2-(α-bromoacetyl) imidazole and 3,4-diethoxythiobenzamide. Then, hydrolysis was conducted in the same manner as in Example 2 to obtain 2-(3,4-diethoxyphenyl)-4-(5-carboxy-2-imidazolyl)thiazole.

EXAMPLE 82

A reaction was conducted in the same manner as in Example 1, by using 4-fluoro-6-ethoxycarbonyl-2-(α-bromoacetyl)pyridine and 3,4-diethoxythiobenzamide. Then, hydrolysis was conducted in the same manner as in Example 2 to obtain 2-(3,4-diethoxyphenyl)-4-(4-fluoro-6-carboxy-2-pyridyl)thiazole.

EXAMPLE 83

A reaction was conducted in the same manner as in Example 1, by using 4-methoxy-6-ethoxycarbonyl-2-(α-bromoacetyl)pyridine and 3,4-diethoxythiobenzamide. Then, hydrolysis was conducted in the same manner as in Example 2 to obtain 2-(3,4-diethoxyphenyl)-4-(4-methoxy-6-carboxy-2-pyridyl)thiazole.

EXAMPLE 84

A reaction was conducted in the same manner as in Example 1, by using 4-hydroxy-6-ethoxycarbonyl-2-(α-bromoacetyl)pyridine and 3,4-diethoxythiobenzamide. Then, hydrolysis was conducted in the same manner as in Example 2 to obtain 2-(3,4-diethoxyphenyl)-4-(4-hydroxy-6-carboxy-2-pyridyl)thiazole.

EXAMPLE 85

A reaction was conducted in the same manner as in Example 1, by using 4-amino-6-ethoxycarbonyl-2-(α-bromoacetyl)pyridine and 3,4-diethoxythiobenzamide. Then, hydrolysis was conducted in the same manner as in Example 2 to obtain 2-(3,4-diethoxyphenyl)-4-(4-amino-6-carboxy-2-pyridyl)thiazole.

EXAMPLE 86

A reaction was conducted in the same manner as in Example 1, by using 4-dimethylamino-6-ethoxycarbonyl-2-(α–bromoacetyl)pyridine and 3,4-diethoxythiobenzamide. Then, hydrolysis was conducted in the same manner as in Example 2 to obtain 2-(3,4-diethoxyphenyl)-4-(4-dimethylamino-6-carboxy-2-pyridyl)thiazole.

EXAMPLE 87

A reaction was conducted in the same manner as in Example 1, by using 4,6-diethoxycarbonylamino-2-(α-bromoacetyl)pyridine and 3,4-diethoxythiobenzamide. Then, hydrolysis was conducted in the same manner as in Example 2 to obtain 2-(3,4-diethoxyphenyl)-4-(4,6-dicarboxy-2-pyridyl)thiazole.

A light yellow amorphous $^1$H-NMR (DMSO-$d_6$) δ ppm: 1.39(3H, t, J=6.8 Hz), 1.41(3H, t, J=6.8 Hz), 4.10(2H, q, J=6.8 Hz), 4.18(2H, q, J=6.8Hz), 7.12(1H, d, J=8.4 Hz), 7.57(1H, s), 7.6(1H, d, J=8.4 Hz), 8.36(1H, d, J=1.4 Hz), 8.73(1H, d, J=1.4 Hz), 13.75(1H, brs)

EXAMPLE 88

A reaction was conducted in the same manner as in Example 1, by using 6-(4-methyl-1-piperazinyl)-2-(α-bromoacetyl)pyridine and 3,4-diethoxythiobenzamide, to obtain 2-(3,4-diethoxyphenyl)-4-[6-(4-methyl-1-piperazinyl)-2-pyridyl]thiazole trihydrochloride.

A yellow needle (recrystallized from ethanol-diethyl ether) m.p.: 230°–234° C.

EXAMPLE 89

A reaction was conducted in the same manner as in Example 1, by using 6-morpholino-2-(α-bromoacetyl)-pyridine and 3,4-diethoxythiobenzamide, to obtain 2-(3,4-diethoxyphenyl)- 4-(6-morpholino-2-pyridyl)thiazole hydrochloride.

A yellow needle (recrystallized from ethanol-diethyl ether) m.p.: 125°–128° C.

EXAMPLE 90

A reaction was conducted in the same manner as in Example 1, by using 6-(1,2,4-triazol-1-yl)-2-(α-bromoacetyl)pyridine and 3,4-diethoxythiobenzamide, to obtain 2-(3,4-diethoxyphenyl)-4-[6-(1,2,4-triazol-1-yl)-2-pyridyl]thiazole.

A light yellow needle (recrystallized from ethanol) m.p.: 164°–166° C.

EXAMPLE 91

A reaction was conducted in the same manner as in Example 1, by using 6-(2-carboxy-1-pyrrolidinyl)-2-(α-bromoacetyl)pyridine and 3,4-diethoxythiobenzamide, to obtain 2-(3,4-diethoxyphenyl)-4-[6-(2-carboxy-1-pyrrolidinyl)-2-pyridyl]thiazole.

A yellow powder (recrystallized from ethanol-diethyl ether) m.p.: 170°–171° C.

EXAMPLE 92

A reaction was conducted in the same manner as in Example 1, by using 6-(2-carboxyethylamino)-2-(α-bromoacetyl)pyridine and 3,4-diethoxythiobenzamide, to obtain 2-(3,4-diethoxyphenyl)-4-[6-(2-carboxyethylamino)-2-pyridyl]thiazole.

EXAMPLE 93

A reaction was conducted in the same manner as in Example 1, by using 4-(2-dimethylaminoethylamino)-2-(α-bromoacetyl)pyridine and 3,4-diethoxythiobenzamide, to obtain 2-(3,4-diethoxyphenyl)-4-[4-(2-dimethylaminoethylamino)-2-pyridyl]thiazole trihydrochloride.

A light yellow powder (recrystallized from ethanol diethyl ether) m.p.: 240°–243° C. (decomp.)

EXAMPLE 94

A reaction was conducted in the same manner as in Example 1, by using 6-(2-carboxyethoxy)-2-(α-bromoacetyl)pyridine and 3,4-diethoxythiobenzamide, to obtain 2-(3,4-diethoxyphenyl)-4-[6-(2-carboxyethoxy)-2-pyridyl]thiazole.

EXAMPLE 95

A reaction was conducted in the same manner as in Example 1, by using 6-(2-carboxyethylthio)-2-(α-bromoacetyl)pyridine and 3,4-diethoxythiobenzamide, to obtain 2-(3,4-diethoxyphenyl)-4-[6-(2-carboxyethylthio)-2-pyridyl]thiazole.

EXAMPLE 96

A reaction was conducted in the same manner as in Example 1, by using 6-(1-phenyl-1-hydroxymethyl)-2-(α-bromoacetyl)pyridine and 3,4-diethoxythiobenzamide, to obtain 2-(3,4-diethoxyphenyl)-4-[6-(1-phenyl-1-hydroxymethyl)-2-pyridyl]thiazole.

EXAMPLE 97

A reaction was conducted in the same manner as in Example 1, by using 6-(1,2-dihydroxyethyl)-2-(α-bromoacetyl)pyridine and 3,4-diethoxythiobenzamide, to obtain 2-(3,4-diethoxyphenyl)-4-[6-(1,2-dihydroxyethyl)-2-pyridyl]thiazole.

A white needle (recrystallized from ethyl acetate-n-hexane)

m.p.: 112°–112.2° C.

EXAMPLE 98

A reaction was conducted in the same manner as in Example 1, by using 4-carboxy-6-ethoxycarbonyl-2-(α-bromoacetyl)pyridine and 3,4-diethoxythiobenzamide, to obtain 2-(3,4-diethoxyphenyl)-4-(4-carboxy-6-ethoxycarbonyl-2-pyridyl)thiazole.

A white powder (recrystallized from ethanol)

m.p.: 188°–189° C.

$^1$H-NMR (CDCl$_3$) δ ppm: 1.37–1.66(9H, m), 4.17(2H, q, J=7.1 Hz), 4.24(2H, q, J=7.1 Hz), 4.53(2H, q, J=7.4 Hz), 6.94(1H, d, J=8.7 Hz), 7.57(1H, d, J=8.7 Hz), 7.63(1H, s), 8.30(1H, s), 8.60(1H, s), 8.99(1H, s)

The following compounds were obtained in the same manner as in Example 1, by using appropriate starting materials.

[TABLE 18]

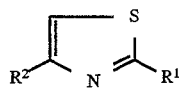

| Compound of Example 99 |
|---|
| R$^1$ = C$_2$H$_5$O 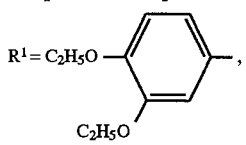, R$^2$ = 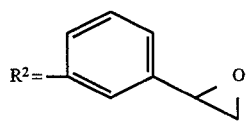 |
| Crystal form: white solid |
| Salt form: free |

[TABLE 18]-continued

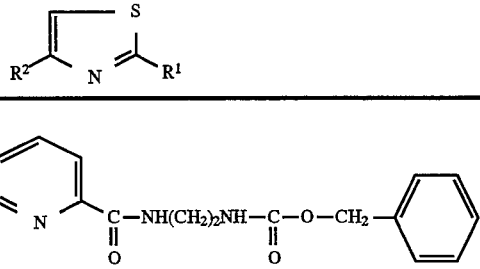

Compound of Example 100
$R^1 = C_2H_5O$-phenyl(-OC_2H_5),
$R^2 =$ pyridyl-C(=O)-NH(CH_2)_2NH-C(=O)-O-CH_2-phenyl
Crystal form: colorless needle
m.p.: 161–162° C.
Recrystallization solvent: ethyl acetate
Salt form: free

Compound of Example 101
$R^1 = C_2H_5O$-phenyl(-OC_2H_5),
$R^2 =$ pyridyl-CH(CN)-C(=O)-O-C_2H_5
Crystal form: yellow needle
m.p.: 240.5–242.5° C.
Recrystallization solvent: ethanol-dimethylformamide
Salt form: free

Compound of Example 102
$R^1 = C_2H_5O$-phenyl(-OC_2H_5),
$R^2 =$ phenyl-NH-C(=O)-NH(CH_2)_2-N(morpholine)
Crystal form: white powder
m.p.: 204–205° C.
Recrystallization solvent: acetone
Salt form: hydrochloride

[TABLE 19]

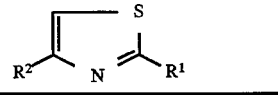

Compound of Example 103
$R^1 = C_2H_5O$-phenyl(-OC_2H_5),
$R^2 =$ pyridyl-C(=S)-NH_2
Crystal form: yellow powder
m.p.: 177.5–178° C.
Recrystallization solvent: ethanol
Salt form: free

Compound of Example 104
$R^1 = C_2H_5O$-phenyl(-OC_2H_5),
$R^2 =$ pyridyl-C(=NH)-SCH_3
Crystal form: yellow powder
m.p.: 174–177° C.
Recrystallization solvent: benzene
Salt form: monomethylsulfate

Compound of Example 105
$R^1 = C_2H_5O$-phenyl(-OC_2H_5),
$R^2 =$ pyridyl-C(=NH)-NH_2
Crystal form: white powder
m.p.: 288–290° C.
Recrystallization solvent: Chloroform-diethyl ether
Salt form: monomethylsulfate

[TABLE 19]-continued

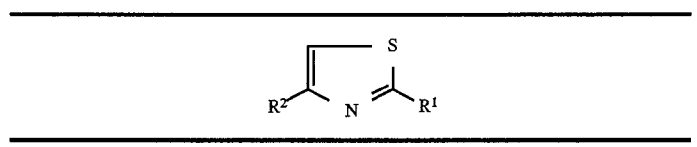

Compound of Example 106

$R^1 = C_2H_5O$ 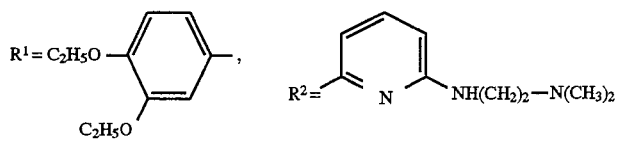, $R^2 =$ (structure with pyridine-NH(CH$_2$)$_2$—N(CH$_3$)$_2$)

Crystal form: light yellow powder
m.p.: 236–237.5° C.

Recrystallization solvent: ethanol-diethyl ether
Salt form: dihydrochloride

[TABLE 20]

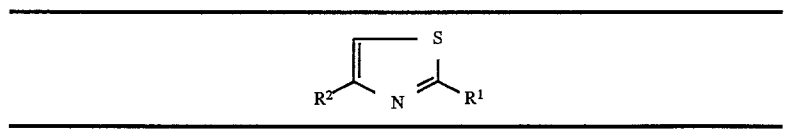

Compound of Example 107

$R^1 = C_2H_5O$ 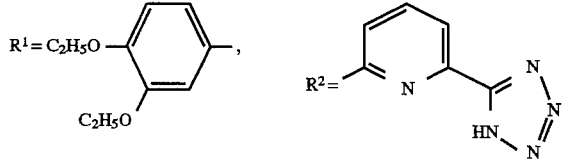, $R^2 =$ (pyridine with tetrazole substituent)

Crystal form: white powder
m.p.: 243–248° C.

Recrystallization solvent: ethanol-ethyl acetate
Salt form: free

Compound of Example 108

$R^1 = C_2H_5O$ 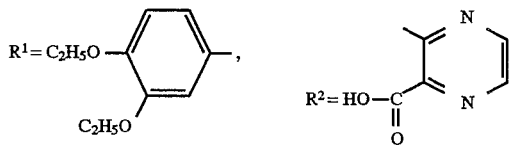, $R^2 = HO-\underset{\underset{O}{\|}}{C}-$ (pyrazine group with methyl)

Crystal form: light brown needle
m.p.: 184–185° C.

Recrystallization solvent: ethyl acetate
Salt form: free

Compound of Example 109

$R^1 = C_2H_5O$ 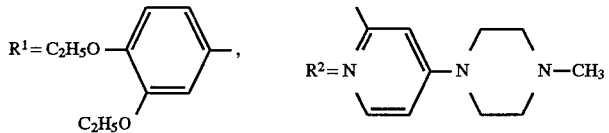, $R^2 = N$ (pyridine)—N(piperazine)N—CH$_3$

Crystal form: yellowish brown powder
m.p.: 234–240° C. (decomp.)

Recrystallization solvent: ethanol-diethyl ether
Salt form: dihydrochloride

Compound of Example 110

$R^1 = C_2H_5O$ 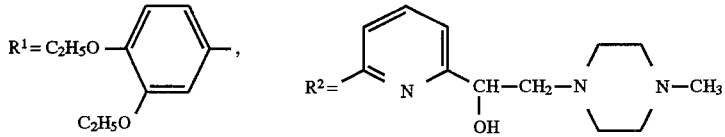, $R^2 =$ (pyridine)—CH(OH)—CH$_2$—N(piperazine)N—CH$_3$ Crystal form: white powder
m.p.: 129–130.8° C.

Recrystallization solvent: diethyl ether
Salt form: free

[TABLE 21]

| | |
|---|---|
| Compound of Example 111 | |
| R¹ = C₂H₅O-phenyl(C₂H₅O)- | R² = pyridine-CH(OH)CH₂N(CH₃)₂ |
| Crystal form: white powder<br>m.p.: 106–110° C. | Recrystallization solvent:<br>diethyl ether-dichloromethane<br>Salt form: free |
| Compound of Example 112 | |
| R¹ = C₂H₅O-phenyl(C₂H₅O)- | R² = pyridine-CH(N(CH₃)₂)CH₂OH |
| Crystal form: white powder<br>m.p.: 107–109.5° C. | Recrystallization solvent:<br>diethyl ether-n-hexane<br>Salt form: free |
| Compound of Example 113 | |
| R¹ = C₂H₅O-phenyl(C₂H₅O)- | R² = pyridine-C(=NH)NH-OH |
| Crystal form: white powder<br>m.p.: 218–220° C. | Recrystallization solvent:<br>ethyl acetate<br>Salt form: free |
| Compound of Example 114 | |
| R¹ = C₂H₅O-phenyl(C₂H₅O)- | R² = pyridine-C(=NH)O⁻ |
| Crystal form: light yellow powder<br>m.p.: 254–257° C. | Recrystallization solvent:<br>dichloromethane<br>Salt form: sodium salt (Na⁺) |

[TABLE 22]

| | |
|---|---|
| Compound of Example 115 | |
| R¹ = C₂H₅O-phenyl(C₂H₅O)- | R² = pyrimidine N-oxide |
| Crystal form: light brown prism | Recrystallization solvent:<br>ethyl acetate<br>Salt form: free |
| Compound of Example 116 | |
| R¹ = C₂H₅O-phenyl(C₂H₅O)- | R² = pyrazine di-N-oxide |
| Crystal form: light yellow needle<br>m.p.: 205–206° C. | Recrystallization solvent:<br>chloroform-ethyl acetate<br>Salt form: free |

[TABLE 22]-continued

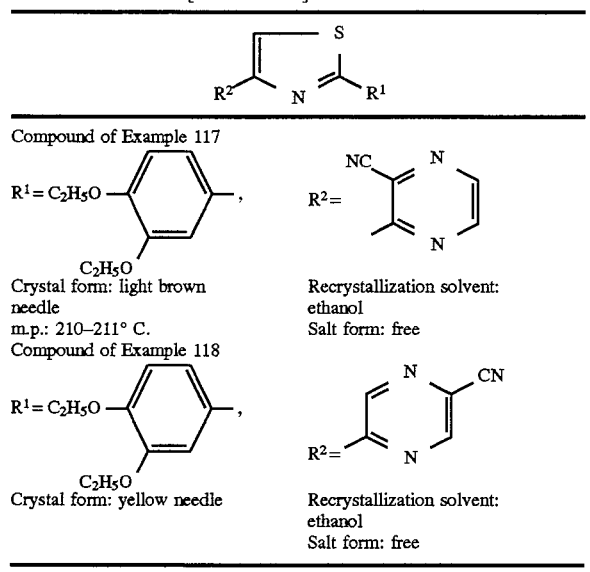

[TABLE 23]

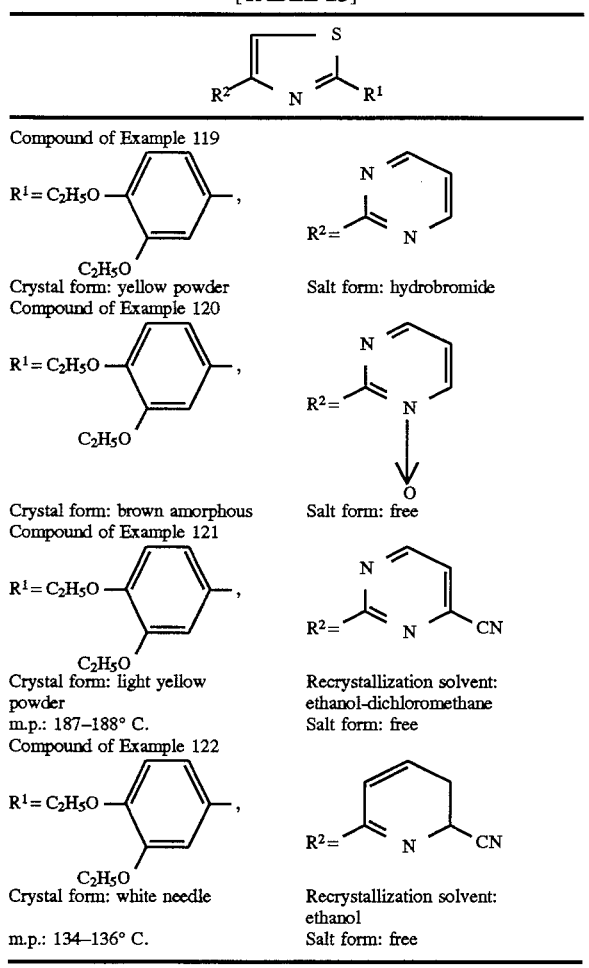

The NMR data of the compounds of Examples 99, 115, 118, 119 and 120 are as follows.
Compound of Example 99
$^1$H-NMR (CDCl$_3$) δ ppm: 1.45–1.54(6H, m), 2.98–3.01 (1H, m), 3.18–3.22(1H, m), 4.06–4.09(1H, m), 4.10(2H, q, J=7.0 Hz), 4.19(2H, q, J=7.0 Hz), 6.89(1H, d, J=8.4 Hz), 7.14(1H, dd, J=0.9 Hz, 7.8 Hz), 7.50(1H, dd, J=2.1 Hz, 8.4 Hz), 7.62(1H, d, J=2.1 Hz), 7.73(1H, t, J=7.8 Hz), 8.06(1H, s), 8.16(1H, dd, J=0.9 Hz, 7.8 Hz)

Compound of Example 115
$^1$H-NMR (CDCl$_3$) δ ppm: 1.50(3H, t, J=6.8 Hz), 1.53(3H, t, J=6.8 Hz), 4.17(2H, q, J=6.8 Hz), 4.22(1H, d, J=6.8 Hz), 6.93(1H, d, J=8.4 Hz), 7.48(1H, dd, J=2,1 Hz, 8.4 Hz), 7.62(1H, d, J=2.1 Hz), 8.04(1H, dd, J=1.6 Hz, 4.0 Hz), 8.12(1H, s), 8.44(1H, d, J=4.0 Hz), 9.06(1H, d, J=1.6 Hz)

Compound of Example 118
$^1$H-NMR (CDCl$_3$) δ ppm: 1.51(3H, t, J=7.0 Hz), 1.52(3H, t, J=7.0 Hz) 4.18 (2H, q, J=7.0 Hz), 4.24(2H, q, J=7.0 Hz), 6.95(1H, d, J=8.4 Hz), 7.54(1H, d, J=2.1 Hz, 8.4 Hz), 7.62(1H, d, J=2.1 Hz), 8.21(1H, s), 8.83(1H, s), 9.68(1H, s)

Compound of Example 119
$^1$H-NMR (CDCl$_3$) δ ppm: 1.50(3H, t, J=7.0 Hz), 1.51(3H, t, J=7.0 Hz), 4.15(2H, q, J=7.0 Hz), 4.31(2H, q, J=7.0 Hz), 6.92(1H, d, J=8.4 Hz), 7.57(1H, dd, J=2.1 Hz, 8.4 Hz), 7.64(1H, t, J=5.2 Hz), 7.90(1H, d, J=2.1 Hz), 8.53(1H, s), 9.17(2H, d, J=5.2 Hz)

Compound of Example 120
$^1$H-NMR (CDCl$_3$) δ ppm: 1.45–1.52(6H, m), 4.09–4.27 (4H, m), 6.89(1H, d, J=8.4 Hz), 7.23–7.63(4H, m), 8.50–8.56(1H, m), 9.51(1H, s)

EXAMPLE 123

A reaction was conducted in the same manner as in Example 1, by using 6-(1-carboxy-1-hydroxymethyl)-2-(α-bromoacetyl)pyridine and 3,4-diethoxythiobenzamide, to obtain 2-(3,4-diethoxyphenyl)-4-[6-(1-carboxy-1-hydroxymethyl)-2-pyridyl]thiazole.

EXAMPLE 124

880 mg of trimethylsulfonium iodide was added to a suspension of 172 mg of 60% sodium hydride in 15 ml of dimethyl sulfoxide. The mixture was subjected to a reaction at room temperature for 1 hour. Thereto was dropwise added a solution of 1 g of 2-(3,4-diethoxyphenyl)-4-(6-formyl-2-pyridyl)thiazole dissolved in 20 ml of dimethyl sulfoxide. The mixture was stirred overnight at room temperature. The reaction mixture was poured into 150 ml of ice water. The mixture was subjected to extraction three times with 200 ml of ethyl acetate. The ethyl acetate layer was water-washed and dried over anhydrous sodium sulfate. The solvent was removed. The residue was purified by silica gel column chromatography (elutant: n-hexane/ethyl acetate=4/1) to obtain 760 mg of 2-(3,4-diethoxyphenyl)-4-(6-oxiranyl-2-pyridyl)thiazole.

A white solid
$^1$H-NMR (CDCl$_3$) δ ppm: 1.45–1.54(6H, m), 2.98–3.01 (1H, m), 3.18–3.22(1H, m), 4.06–4.09(1H, m), 4.10(2H, q, J=7.0 Hz), 4.19(2H, q, J=7.0 Hz), 6.89(1H, d, J=8.4 Hz), 7.14(1H, dd, J=0.9 Hz, 7.8 Hz), 7.50(1H, dd, J=2.1 Hz, 8.4 Hz), 7.62(1H, d, J=2.1 Hz), 7.73(1H, t, J=7.8 Hz), 8.06(1H, s), 8.16(1H, dd, J=0.9 Hz, 7.8Hz)

EXAMPLE 125

A solution of 505 mg of potassium hydroxide dissolved in 30 ml of water was added to a solution of 700 mg of 2-(3,4-diethoxyphenyl)-4-(6-oxiranyl-2-pyridyl)thiazole dissolved in 30 ml of dimethyl sulfoxide. The mixture was stirred at 100° C. for 7 hours. The reaction mixture was subjected to extraction three times with 50 ml of ethyl acetate. The ethyl acetate layer was dried over anhydrous sodium sulfate. The solvent was removed by distillation. The residue was purified by silica gel column chromatography (elutant: dichloromethane/methanol=20/1) and then recrystallized from ethyl acetate-n-hexane to obtain 350 mg of 2-(3,4-diethoxyphenyl)-4-[6-(1,2-dihydroxyethyl)-2-pyridyl]-thiazole.

A white needle m.p.: 112°–112.2° C.

EXAMPLE 126

A solution of 38.5 g of metachloroperbenzoic acid (80%) dissolved in 400 ml of methylene chloride was dropwise added, with ice cooling, to a solution of 49.6 g of 2-(3,4-diethoxyphenyl)-4-(2-pyridyl)thiazole dissolved in 250 ml of methylene chloride. The mixture was stirred at room temperature for 2 hours. To the reaction mixture was added an aqueous sodium hydrogencarbonate solution, followed by separation of layers. The organic layer was washed with an aqueous sodium hydrogencarbonate solution and dried over anhydrous magnesium sulfate. The solvent was removed by distillation. The residue was recrystallized from ethyl acetate to obtain 45.2 g of 2-[2-(3,4-diethoxyphenyl)-4-thiazolyl]pyridine-1-oxide.

A light yellow needle m.p.: 121°–123.5° C.

The compounds of Examples 21, 38, 39, 115, 116 and 120 were obtained in the same manner as in Example 126, by using appropriate starting materials.

EXAMPLE 127

A mixture of 3 g of 2-[2-(3,4-diethoxyphenyl)-4-thiazolyl]pyridine-1-oxide, 2.6 g of methyl cyanoacetate and 150 ml of acetic anhydride was stirred at 110° C. for 4 hours and then allowed to cool. The resulting crystals were collected by filtration and recrystallized from ethanol-dimethylformamide to obtain 2.1 g of 2-(3,4-diethoxyphenyl)-4-[6-(1-methoxycarbonyl-1-cyanomethyl)-2-pyridyl]thiazole.

A yellow needle m.p.: 240.5°–242.5° C.

EXAMPLE 128

21.3 ml of triethylamine and 30.7 ml of cyanotrimethylsilane were added to a suspension of 26.3 g of 2-[2-(3,4-diethoxyphenyl)-4-thiazolyl]pyridine-1-oxide in 500 ml of acetonitrile. The mixture was refluxed for 62 hours. The solvent in the reaction mixture was removed by distillation. To the residue was added an aqueous sodium carbonate solution. The mixture was subjected to extraction with methylene chloride. The methylene chloride layer was dried over anhydrous magnesium sulfate. The solvent was removed by distillation. The residue was purified by silica gel column chromatography (elutant: methylene chloride) and recrystallized from ethanol to obtain 22.2 g of 2-(3,4-diethoxyphenyl)-4-(6-cyano-2-pyridyl)thiazole.

A white needle m.p.: 134°–136° C.

The compounds of Examples 43, 117, 118 and 121 were obtained in the same manner as in Example 128, by using appropriate starting materials.

EXAMPLE 129

280 mg of ammonium chloride and 380 mg of sodium azide were added to a solution of 1.5 g of 2-(3,4-diethoxyphenyl)-4-(6-cyano-2-pyridyl)thiazole dissolved in 30 ml of dimethylformamide. The mixture was stirred at 120° C. for 9 hours. To the reaction mixture was added diluted hydrochloric acid to make the mixture acidic, followed by extraction three times with 150 ml of ethyl acetate. The ethyl acetate layer was dried over anhydrous sodium sulfate. The solvent was removed by distillation. The residue was recrystallized from ethanol-ethyl acetate to obtain 1.19 g of 2-(3,4-diethoxyphenyl)-4-[6-(1,2,3,4-tetrazol-5-yl)-2-pyridyl]thiazole.

A white powder m.p.: 243°–248° C.

The compound of Example 13 was obtained in the same manner as in Example 129, by using appropriate starting materials.

EXAMPLE 130

10.1 g of 2-(3,4-diethoxyphenyl)-4-(6-cyano-2pyridyl) thiazole, 6.48 g of thioacetamide and a 25% hydrochloric acid-DMF solution (100 ml) were stirred at 100°–110° C. for 3 hours. The reaction mixture was poured into 500 ml of ice water. Thereto was added 1.0 liter of ethyl acetate. The resulting precipitate (insolubles) were removed by filtration. The filtrate was subjected to layer separation, and extraction with 500 ml of ethyl acetate was conducted. The extract was washed with water and a saturated aqueous sodium chloride solution and dried over anhydrous magnesium sulfate. The solvent was removed by distillation. The residue was recrystallized from ethanol to obtain 10.2 g of 2-(3,4-diethoxyphenyl)-4-(6-carbothioamido-2-pyridyl)thiazole.

A yellow powder m.p.: 177.5°–178° C.

EXAMPLE 131

0.34 ml of dimethyl sulfate was added to a suspension of 1.08 g of 2-(3,4-diethoxyphenyl)-4-(6-carbothioamido-2-pyridyl)thiazole. The mixture was refluxed for 45 minutes and then allowed to cool. The resulting crystals were collected by filtration and recrystallized form benzene to obtain 1.09 of 2-(3,4-diethoxyphenyl)-4-[6-(1-imino-1-methylthiomethyl)-2-pyridyl]thiazole monomethylsulfate.

A yellow powder m.p.: 174°–177° C.

EXAMPLE 132

0.81 g of 2-(3,4-diethoxyphenyl)-4-[6-(1-imino-1-methylthiomethyl)-2-pyridyl]thiazole monomethylsulfate and a saturated ammonia-methanol solution were refluxed at 100° C. for 3 hours in a sealed tube. The solvent was removed by distillation. The residue was recrystallized from chloroform-diethyl ether to obtain 0.44 g of 2-(3,4-diethoxyphenyl)-4-(6-amidino-2-pyridyl)thiazole monomethylsulfate.

A white powder m.p.: 288°–290° C.

EXAMPLE 133

278 mg of hydroxylamine hydrochloride was added, with ice cooling, to a suspension of 1.55 g of 2-(3,4-diethoxyphenyl)-4-[6-(1-imino-1-methylthiomethiazole in 40 ml of methanol. The mixture was stirred at room temperature for 14 hours. The solvent in the reaction mixture was removed by distillation. To the residue was added water. The mixture was made alkaline with a 5N aqueous sodium hydroxide solution. The resulting crystals were collected by filtration and recrystallized from ethyl acetate to obtain 1.03 g of 2-(3,4-diethoxyphenyl)-4-[6-(N'-hydroxyamidino)-2-pyridyl]thiazole.

A white powder m.p.: 218°–220° C.

EXAMPLE 134

2.4 g of a 50% aqueous dimethylamine solution was added to a solution of 1 g of 2-(3,4-diethoxyphenyl)-4-(6- oxiranyl-2-pyridyl)thiazole dissolved in 200 ml of methanol. The mixture was refluxed overnight. The resulting precipitate was removed by filtration. The filtrate was concentrated. The concentrate was purified by silica gel column chromatography (elutant: dichloromethane/methanol=20/1) and silica gel thin-layer chromatography and then recrystallized from diethyl ether-dichloromethane to obtain 140 mg of 2-(3,4-diethoxyphenyl)-4-[6-(1-hydroxy-2-dimethylaminoethyl)-2-pyridyl]thiazole (A). Further, recrystallization from diethyl ether-n-hexane was conducted to obtain 28 mg of 2-(3,4-diethoxyphenyl)-4-[6-(1-dimethylamino-2-hydroxyethyl)-2-pyridyl]thiazole (B).

(A): a white powder and m.p.=106°–110° C.

(B): a white powder and m.p.=107°–109.5° C.

The compound of Example 110 was obtained in the same manner as in Example 134, using appropriate starting materials.

Pharmacological Tests

The pharmacological tests for present compounds were conducted according to the following method.

Activity for inhibiting the generation of $O_2^-$ in human neutrophilic leukocyctes Human neutrophilic leukocyctes were prepared in accordance with the method of M. Markert et al. [Methods in Enzymology, vol. 105; pp. 358–365 (1984)]. That is, a whole blood obtained from a healthy adult and treated by anticoagulation method was subjected to a dextran-hypotonic treatment to obtain leukocyte cells. The leukocyte cells were then subjected to a density gradient ultracentrifugation by Ficoll-Paque to obtain a neutrophilic leukocyte fraction.

$O_2^-$ generation was examined by the ferricyto-chrome C method in accordance with the method of B. N. Cronstein et al. [Journal of Experimental Medicine, vol. 158, pp. 1160–1177 (1983)]. That is, $1 \times 10^{-6}$ cell of neutrophilic leukocytes were stimulated with $3 \times 10^{-7} M$ of N-formyl-L-methionyl-L-leucyl-L-phenylalanine (FMLP) at 37° C. in the presence of 1.3 mg/ml of ferricytochrome C and 5 μg/ml of cytochalasin B in a Hepes-buffered Hank's solution (pH 7.4); the amount of ferricytochrome C formed by 4 minutes of reduction was determined by measuring an absorbance at a wavelength of 550 nm using a spectrophotometer; an absorbance in the presence of 25.1 μg/ml of superoxide dismutase (SOD) was also measured; the difference of the two absorbances was taken as the amount of $O_2^-$ generated. Each test compound was dissolved in dimethyl sulfoxide (DMSO); the solution was added to neutrophilic leukocytes before the addition of FMLP; then, the neutrophilic leukocytes were pre-incubated at 37° C. for 20 minutes. By using the amount of $O_2^-$ generated when the test compound solution was added and the amount of $O_2^-$ generated when only the solvent (DMSO) was added, a ratio of inhibition (%) was calculated, and the activity for inhibiting $O_2^-$ generation was expressed as 50% inhibitory concentration ($IC_{50}$).

Test compounds 1. 2-(3,4-Diethoxyphenyl)-4-[4-(2-hydroxyethoxy)-3-carboxyphenyl]thiazole
2. 5-[2-(3,4-Diethoxyphenyl)-4-thiazole]-2-hydroxybenzenecarbohydroxamic acid
3. 2-(3,4-Diethoxyphenyl)-4-(4-carbamoylphenyl)thiazole
4. 2-(3,4-Diethoxyphenyl)-4-(2-carboxy-3-hydroxy-6-pyridyl)thiazole
5. 2-(3,4-Diethoxyphenyl)-4-[3-(1,2,3,4-tetrazol-5-yl)-4-hydroxyphenyl]thiazole
6. 2-(3,4-Diethoxyphenyl)-4-(4-carboxymethylaminocarbonylphenyl]thiazole
7. 4-[2-(3,4-Diethoxyphenyl)-4-thiazolyl]benzenecarbohydroxamic acid
8. 2-(3,4-Diethoxyphenyl)-4-(3-carbazoyl-4-hydroxyphenyl)thiazole
9. 2-(3,4-Diethoxyphenyl)-4-(4-carbazoylphenyl)thiazole
10. 5-[2-(3,4-Diethoxyphenyl)-4-thiazolyl]-2-hydroxy-3-(2-methyl-2-propenyl)benzenehydroxamic acid
11. 2-(3,4-Diethoxyphenyl)-4-(2-hydroxymethyl-4-methyl-6-pyridyl)thiazole
12. 2-(3,4-Diethoxyphenyl)-4-(1-oxo-2-hydroxymethyl-4-methyl-6-pyridyl)thiazole
13. Disodium [2-(3,4-dimethoxyphenyl)-4thiazolyl] salicylhydroxamate
14. 5-[2-(3,4-Diethoxyphenyl)-4-thiazolyl]-2-hydroxy-3-methylbenzenehydroxamic acid
15. Ethyl [2-(3,4-diethoxyphenyl)-4-thiazolyl]benzenehydroxamate
16. 1-{3-[2-(3,4-Dimethoxyphenyl)-4-thiazolyl]phenyl}-2-methylisothiourea hydroiodide
17. 2-(3,4-Diethoxyphenyl)-4-(4-carbothioamidophenyl)thiazole
18. 2-(3,4-Diethoxyphenyl)-4-(N'-hydroxyamidinophenyl)thiazole
19. 2-(3,4-Diethoxyphenyl)-4-[4-(1-imino-1-methylthiomethyl)phenyl]thiazole monomethylsulfate
20. 1-{4-[(3,4-Diethoxyphenyl)-4-thiazolyl]phenyl}thiourea
21. 4-[2-(3,4-Diethoxyphenyl)-4-thiazolyl]benzhydrazide hydrochloride
22. 2-Methyl-1-{4-[2-(3,4-diethoxyphenyl)-4-thiazolyl]}benzoisothiourea monomethylsulfate
23. 2-(3,4-Diethoxyphenyl)-4-(2-pyrazinyl)thiazole
24. 2-(3,4-Diethoxyphenyl)-4-(6-carbothioamido-2-pyridyl)thiazole
25. 2-(3,4-Diethoxyphenyl)-4-[6-(1-imino-1-methylthiomethyl)-2-pyridyl]thiazole monomethylsulfate
26. 2-(3,4-Diethoxyphenyl)-4-[6-(1,2,3,4-tetrazol-5-yl)-2-pyridyl]thiazole
27. 2-(3,4-Diethoxyphenyl)-4-[4-(4-methyl-1-piperazinyl)-2-pyridyl]thiazole dihydrochloride
28. 2-(3,4-Diethoxyphenyl)-4-{6-[2-(4-methyl-1-piperazinyl)-1-hydroxyethyl]-2-pyridyl}thiazole
29. 2-(3,4-Diethoxyphenyl)-4-[6-(N'-hydroxyamidino)-2-pyridyl]thiazole
30. Sodium 2-[2-(3,4-diethoxyphenyl)-4-thiazolyl]-6-pyrimidylcarboxylate The results are shown in Table 24.

TABLE 24

| Test compound | $TC_{50}$ (μM) | Test compound | $IC_{50}$ (μM) |
|---|---|---|---|
| 1 | 0.16 | 16 | 0.046 |
| 2 | 0.037 | 17 | 0.066 |
| 3 | 0.0062 | 18 | 0.013 |
| 4 | 0.2 | 19 | 0.2 |
| 5 | 0.27 | 20 | 0.03 |
| 6 | 0.14 | 21 | 0.17 |
| 7 | 0.042 | 22 | 0.6 |
| 8 | 0.1 | 23 | 0.072 |
| 9 | 0.037 | 24 | 0.055 |
| 10 | 0.065 | 25 | 0.33 |
| 11 | 0.18 | 26 | 0.35 |
| 12 | 0.42 | 27 | 0.75 |
| 13 | 0.24 | 28 | 0.45 |
| 14 | 0.072 | 29 | 0.23 |
| 15 | 0.29 | 30 | 0.6 |

We claim:

1. A thiazole derivative of the formula (1):

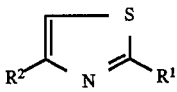

wherein, $R^1$ is a phenyl group which may have from 1–3 lower alkoxy groups as substituents on the phenyl ring; $R^2$ is a group of the formula:

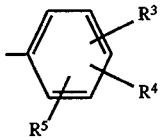

(wherein, $R^3$ is a carboxyl group, a lower alkoxycarbonyl group, a hydroxyl group-substituted lower alkyl group, a lower alkoxy group, a tri-lower alkyl-substituted silyloxy group, a hydroxyl group or a hydrogen atom; $R^4$ is a hydrogen atom, a lower alkenyl group or a lower alkyl group; and $R^5$ is an amino-lower alkoxycarbonyl group which may have at least one lower alkyl group as a substituent, an amino-lower alkoxy-substituted lower alkyl group which may have at least one lower alkyl group as a substituent, an amino-lower alkoxy group which may have at least one lower alkyl group as a substituent, a lower alkoxy group having at least one tetrahydropyranyloxy group or at least one hydroxyl group, a phenylsulfonyloxy group-substituted lower alkoxy group which may have at least one lower alkyl group as a substituent on the phenyl ring, a hydroxysulfonyl group, an amino-lower alkanoyloxy-substituted lower alkyl group which may have at least one lower alkyl group as a substituent, a lower alkynyloxy group, a group —(CO)$_l$—NHR$^6$ (wherein l is 0 or 1 and $R^6$ is a hydroxyl group; a phenyl-lower alkyl group; a carboxyl group-substituted lower alkyl group; an amino group; an aminothiocarbonyl group which may have at least one benzoyl group an amidino group; a group of the formula:

(wherein $R^7$ is a lower alkylthio group or a morpholino-lower alkylamino group); or a phenyl-lower alkoxycarbonyl group-substituted lower alkyl group), or $R^5$ is an amino-substituted lower alkanoyloxy-lower alkyl group which may have at least one lower alkyl group as a substituent, an aminothiocarbonyl group, a group of the formula:

(wherein $R^8$ is a hydroxyimino group, a lower alkylthio group, a hydrazino group, a lower alkoxy group, a piperazinyl group which may have at least one lower alkyl group, a morpholino group or a morpholino-lower alkylamino group), or $R^5$ is a 1,2,3,4-tetrazolyl group or a 1,3,4-oxadiazolyl group which may have at least one oxo group); and a salt thereof;

provided that when $R^3$ and $R^4$ are both hydrogen atoms and $R^5$ is —(CO)$_l$—NHR$^6$ and l is 0, then $R^6$ can not be an aminothiocarbonyl group;

provided further that when $R^3$ is a hydrogen atom, a hydroxide group or a lower alkoxyl group and $R^4$ is a hydrogen atom or a lower alkyl group, then $R^5$ can not be an amino-lower alkoxy group which may have at least one lower alkyl group as a substituent.

2. A thiazole derivative or a salt thereof according to claim 1, wherein $R^3$ is a hydrogen atom or a hydroxyl group.

3. A thiazole derivative or a salt thereof according to claim 1, wherein $R^3$ is a carboxyl group, a lower alkoxycarbonyl group, a hydroxyl group-substituted lower alkyl group, a lower alkoxy group or a tri-lower alkyl-substituted silyloxy group.

4. A thiazole derivative or a salt thereof according to claim 2, wherein $R^4$ is a hydrogen atom.

5. A thiazole derivative or a salt thereof according to claim 2, wherein $R^4$ is a lower alkenyl group or a lower alkyl group.

6. A thiazole derivative or a salt thereof according to claim 4 or 5, wherein $R^5$ is a group of the formula: —(CO)l—NHR$^6$ ($R^6$ and l are the same as defined in claim 1) or a 1,2,3,4-tetrazolyl group.

7. 2-Hydroxy-5-[2-(3,4-diethoxyphenyl)thiazol-4-yl]benzenecarbohydroxamic acid.

8. 2-(3,4-Diethoxyphenyl)-4-[4-hydroxy-3-(1,2,3,4-tetrazol-5-yl)phenyl]thiazole.

9. 2-(3,4-Diethoxyphenyl)-4-(4-hydroxy-3-carbazoylphenyl)thiazole.

10. A thiazole derivative or a salt thereof according to claim 4 or 5, wherein $R^5$ is an amino-lower alkoxy-carbonyl group which may have at least one lower alkyl group as a substituent, an amino-lower alkoxy-substituted lower alkyl group which may have at least one lower alkyl group as a substituent, an amino-lower alkoxy group which may have at least one lower alkyl group as a substituent, a lower alkoxy group having at least one tetrahydropyranyloxy group or at least one hydroxyl group, a phenylsulfonyloxy group-substituted lower alkoxy group which may have at least one lower alkyl group as a substituent on the phenyl ring, a hydroxysulfonyl group, an amino-lower alkanoyloxy-substituted lower alkyl group which may have at least one lower alkyl group as a substituent, a lower alkynyloxy group, an amino-substituted lower alkanoyloxy-lower alkyl group which may have at least one lower alkyl group as a substituent, an aminothiocarbonyl group, a group of the formula:

or a 1,3,4-oxadiazolyl group which may have at least one oxo group.

11. A superoxide radical inhibitor comprising a pharmaceutically acceptable carrier and, as an effective ingredient, a thiazole derivative according to claim 1, represented by general formula (1):

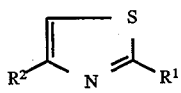

* * * * *